United States Patent [19]
Bandman et al.

[11] Patent Number: 5,965,129
[45] Date of Patent: Oct. 12, 1999

[54] TWO NOVEL HUMAN CATHESPIN PROTEINS

[75] Inventors: Olga Bandman; Roger Coleman, both of Mountain View, Calif.

[73] Assignee: Incyte Pharmaceuticals, Inc., Palo Alto, Calif.

[21] Appl. No.: 09/080,538

[22] Filed: May 18, 1998

Related U.S. Application Data

[62] Division of application No. 08/723,938, Sep. 26, 1996, Pat. No. 5,776,759.

[51] Int. Cl.⁶ .............................. A61K 38/46; C12N 9/64
[52] U.S. Cl. ......................................... 424/94.65; 435/226
[58] Field of Search .......................... 435/226; 424/94.65

[56] References Cited

U.S. PATENT DOCUMENTS 5,501,969  3/1996  Hastings et al. .................... 435/252.33

OTHER PUBLICATIONS

Baldwin, E.T., et al., "Crystal structures of native and inhibited forms of human cathepsin D: Implications for lysosomal targeting and drug design" *Proc. Natl. Acad. Sci.*, 90:6796–6800 (1993).

Becker, M.M., et al., "Cloning and Characterization of the *Schistosoma japonicum* Aspartic Proteinase Involved in Hemoglobin Degradation" *J. Biol. Chem.*, 270:24496–24501 (1995).

Cataldo, A.M., et al., "Gene Expression and Cellular Content of Cathespin D in Alzheimer's Disease Brain: Evidence of Early Up–Regulation of the Endosomal–Lysosomal System" *Neuron*, 14:671–680 (1995).

Cavailles, V., "Cathepsin D gene is controlled by a mixed promoter, and estrogens stimulate only TATA–dependent transcription in breast cancer cells" *Proc. Natl. Acad. Sci.*, 90:203–207 (1993).

Consonni, R., et al., "Further characterization of platelet–aggregating cysteine proteinase activity in thrombotic thrombocytopenic purpura" *BR. J. Haematol.*, 87:321–324 (1994).

Dickinson, A.J., et al., "An Immunohistochemical and Prognostic Evaluation of Cathepsin D Expression in 105 Bladder Carcinomas" *J. Urol.*, 154:237–241 (1995).

Diedrich, J.F., et al., "Neuropathological Changes in Scrapie and Alzheimer's Disease Are Associated with Increased Expression of Apolipoprotein E and Cathepsin D in Astrocytes" *J. Virol.*, 65:4759–4768 (1991).

Evin, G., et al., "Candidate γ–Secretases in the Generation of the Carboxyl Terminus of the Alzheimer's Diseas βA4 Amyloid: Possible Involvement of Cathepsin D" *Biochemistry*, 34:14185–14192 (1995).

Faust, P.L., et al., "Cloning and sequence analysis of cDNA for human cathepsin D" *Proc. Natl. Acad. Sci.*, 82:4910–4914 (1985).

Huisman, W., et al., "Role of Individual Cathepsins in Lysosomal Protein Digestion as Tested by Specific Inhibitors" *Biochim. Biophys. Acta*, 370:297–307 (1974).

Keyszer, G.M., et al., "Comparative Analysis of Cathepsin L, Cathepsin D, and Collagenase Messenger RNA Expression in Synovial Tissues of Patients with Rheumatoid Arthritis and Osteoarthritis, by in situ Hybridization" *Arthritis & Rheum.*, 38:976–984 (1995).

Kopitz J., et al., "Protein catabolism in fribroblasts cultured from patients with mucolipidosis II and other lysosomal disorders" *Biochem. J.*, 295:577–580 (1993).

Liaudet, E., et al., "Transfected Cathepsin D Stimulates High Density Cancer Cell Growth by Inactivating Secreted Growth Inhibitors" *Cell Growth & Differ.*, 6:1045–1052 (1995).

Long, B.J., et al., "Reduced levels of cathepsin D associated with tamoxifen resistance and estrogen independent in the ZR–75–1 human breast cancer cell line" *Cancer Letters*, 99:233–238 (1996).

Mantle, D., et al., "Comparison of cathepsin protease activities in brain tissue from normal cases and cases with Alzheimer's disease, Lewy body dementia, Parkinson's disease and Huntington's disease" *J. Neurol. Sci.*, 131:65–70 (1995).

McKerrow, J.H., "The Proteases and Pathogenicity of Parasitic Protozoa" *Annu. Rev. Microbiol.*, 47:821–53 (1993).

Mizuochi, T., et al., "Both cathepsin B and cathepsin D are necessary for processing of ovalbumin as well as for degradation of class II MHC invariant chain" *Immunol. Letters*, 43:189–193 (1994).

Ritchlin, C., et al., "Sustained and Distinctive Patterns of Gene Activation in Synovial Fibroblasts and Whole Synovial Tissue Obtained from Inflammatory Synovitis" *Scand. J. Immunol.*, 40:292–298 (1994).

Rochefort, H., "Biological and Clinical Significance of Cathepsin D in Breast Cancer" *Acta Oncol.*, 31:125–130 (1992).

Rosenthal, P.J., et al., "A Malarial Cysteine Proteinase is Necessary for Hemoglobin Degradation by *Plasmodium falciparium*" *J. Clin. Invest.*, 82:1560–1566 (1988).

(List continued on next page.)

*Primary Examiner*—Robert A. Wax
*Attorney, Agent, or Firm*—Incyte Pharmaceuticals, Inc.; Leanne C. Price

[57] ABSTRACT

The present invention provides two novel human cathepsin proteins (HCPs) and polynucleotides encoding HCPs. The invention provides for genetically engineered expression vectors and host cells comprising the nucleic acid sequence encoding HCPs. The invention also provides for the production and use of antibodies to HCPs in pharmaceutical compositions for the treatment of disease processes that include cancers, inflammation, metastasis and peptide and proenzyme processing. In addition, the invention provides for the production and use of inhibitors of HSPs in pharmaceutical compositions for the treatment of diseases. The invention also describes diagnostic assays which utilize the polynucleotide to hybridize with the transcripts encoding HCPs. The invention also provides for the use of antisense molecules in pharmaceutical compositions as therapeutics in cancers, inflammation, metastasis and peptide and proenzyme processing.

3 Claims, 17 Drawing Sheets

OTHER PUBLICATIONS

Ross, J.S., et al., "Quantitative Immunohistochemical Determination of Cathepsin D Levels in Prostatic Carcinoma Biopsies" *Am. J. Clinc. Pathol.,* 104:36–41 (1995).

Saftig, P., et al., "Mice deficient for the lysosomal proteinase cathepsin D exhibit progressive atrophy of the intestinal mucosa and profound destruction of lymhpoid cells" *Embo J.,* 14:3599–3608 (1995).

Smith, A.M., et al., "Adult *Schistosoma mansoni* express cathepsin L proteinase activity" *Mol. Biochem. Parasitol.,* 67:11–19 (1994).

Troen, B.R., et al., "Downstream Sequences Mediate Induction of the Mouse Cathepsin L Promoter by Phorbol Esters" *Cell Growth & Differ.,* 2:23–31 (1991).

Mori, K. et al., "Molecular Cloning of a Novel Mouse Aspartic Protease–like Protein That is Expressed Abundantly in the Kidney", *FEBS Letters,* vol. 401, pp. 218–222, Jan. 20, 1997.

Wiederanders et al., J. Biol. Chem. 267: 13703–13713, 1992.

Horst et al., Biochem J. 273: 355–361, 1991.

Joseph et al., J. Clin. Invest. 81: 1621–1629, 1988.

Adams et al., Nature Genetics 4: 373–380, 1993.

```
5' GCC ACC CTG GAG GAG CCA CCC TGG AAC GAC CCC ATG GTG TGC CGG CTC CCC GTG
                                                                            54
    9          18          27          36          45

TCC AAG AAA ACC CTG CTC TGC AGC TTC CAA GTC CTG GAT GAG CTC GGA AGA CAC
 S   K   K   T   L   L   C   S   F   Q   V   L   D   E   L   G   R   H  108
   63          72          81          90          99

GTG CTG CGG AAG GAC TGT GGC CCA GTG GAC ACC AAG GTT CCA GGT GCT GTG
 V   L   R   K   D   C   G   P   V   D   T   K   V   P   G   A   V  162
   117         126         135         144         153

GAG CCC AAG TCA GCC TTT ACT CAG GGC TCA GCC ATG ATT TCT CTG TCC CAA
 E   P   K   S   A   F   T   Q   G   S   A   M   I   S   L   S   Q  216
   171         180         189         198         207

AAC CAT CCA GAC AAC AGA AAC GAG ACT TTC AGC TCA RTC ATT TCC CTG TTG AAT
 N   H   P   D   N   R   N   E   T   F   S   X   I   S   L   L   N  270
   225         234         243         252         261

GAG GAT CCC CTG TCC CAG GAC TTG CCT GTG AAG ATG GCT TCA ATC TTC AAG AAC
 E   D   P   L   S   Q   D   L   P   V   K   M   A   S   I   F   K   N  324
   279         288         297         306         315

TTT GTC ATT ACC TAT AAC CGG ACA TAT GAG TCA AAG GAA GAA GCC CGG TGG CGC
 F   V   I   T   Y   N   R   T   Y   E   S   K   E   E   A   R   W   R  378
   333         342         351         360         369
```

FIGURE 1A

```
CTG TCC GTC TTT GTC AAT AAC ATG CGA GCA CAG AAG ATC CAG GCC CTG GAC
 L   S   V   F   V   N   N   M   R   A   Q   K   I   Q   A   L   D
387         396         405         414         423         432

CGT GGC ACA GCT CAG TAT GGA GTC ACC AAG TTC AGT GAT CTC ACA GAG GAG GAG
 R   G   T   A   Q   Y   G   V   T   K   F   S   D   L   T   E   E   E
441         450         459         468         477         486

TTC CGC ACT ATC TAC CTG AAT ACT CTC CTG AGA AAA GAG CCT GGC AAC AAG ATG
 F   R   T   I   Y   L   N   T   L   L   R   K   E   P   G   N   K   M
495         504         513         522         531         540

AAG GCC AAG TCT GTG GGT GAC CTC GCC CCA GAA TGG GAC TGG AGG AGT
 K   A   K   S   V   G   D   L   A   P   E   W   D   W   R   S
549         558         567         576         585         594

AAG GGG GCT GTC ACA AAA GTC AAA GAC CAG GGC ATG TGT GGC TCC TGC TGG GCC
 K   G   A   V   T   K   V   K   D   Q   G   M   C   G   S   C   W   A
603         612         621         630         639         648

TTC TCA GTC ACA GGC AAT GTG GAG GGC CAG TGG TTT CTC AAC CAG GGG ACC CTG
 F   S   V   T   G   N   V   E   G   Q   W   F   L   N   Q   G   T   L
657         666         675         684         693         702

CTC TCC TCT GAA CAG CAG CTC TTG GAC TGT GAC AAG ATG GAC AAG GCC TGC
 L   S   S   E   Q   Q   L   L   D   C   D   K   M   D   K   A   C
711         720         729         738         747         756
```

```
    765     774     783     792     801     810
ATG GGC GGC TTG CCC TCC AAT GCC TAC TCG GCC ATA AAG AAT TTG GGA GGG CTG
 M   G   G   L   P   S   N   A   Y   S   A   I   K   N   L   G   G   L 819     828     837     846     855     864
GAG ACA GAG GAT GAC TAC AGC TAC CAG GGT CAC ATG CAG TCC TGC AAC TTC TCA
 E   T   E   D   D   Y   S   Y   Q   G   H   M   Q   S   C   N   F   S 873     882     891     900     909     918
GCA GAG AAG GCC AAG GTC TAC ATC AAT GAC TCC GTG GAG CTG AGC CAG AAC GAG
 A   E   K   A   K   V   Y   I   N   D   S   V   E   L   S   Q   N   E 927     936     945     954     963     972
CAG AAG CTG GCA GCC TGG CTG TAC CGC GAG AGA GGC CCA ATC TCC GTG GCC ATC AAT
 Q   K   L   A   A   W   L   Y   R   E   R   G   P   I   S   V   A   I   N 981     990     999    1008    1017    1026
GCC TTT GGC ATG CAG TTT CTC ATT GAC CAC GGG ATC TCC CGC CCT CTC CGA CCC CTC
 A   F   G   M   Q   F   L   I   D   H   G   I   S   R   P   L   R   P   L 1035    1044    1053    1062    1071    1080
TGC AGC CCT TGG CTC ATT GAC CAT GCG GTG TTG CTT GTG GGC TAC GGC AAC CGC
 C   S   P   W   L   I   D   H   A   V   L   L   V   G   Y   G   N   R 1089    1098    1107    1116    1125    1134
TCT GAC GTT CCC TTT TGG GCC ATC AAG AAC AGC TGG GGC ACT GAC TGG GGT GAG
 S   D   V   P   F   W   A   I   K   N   S   W   G   T   D   W   G   E
```

```
     1143             1152             1161             1170             1179             1188
AAG GGT TAC TAC TAC TTG CAT CGC GGG TCC GGG GCC TGT GGC GTG AAC ACC ATG
 K   G   Y   Y   Y   L   H   R   G   S   G   A   C   G   V   N   T   M 1197             1206             1215             1224             1233             1242
GCC AGC TCG GCG GTG GAC TGA GTG GAC CCC AGC TCG GGG CCT GGT GCT
 A   S   S   A   V   D   *

1251             1260             1269             1278             1287             1296
GAT CAG AGT GGC TGC TGC CCC AGC ACA TGT GTC CAG GCC CCT CCC CGG GAG 1305             1314             1323             1332             1341             1350
GTA CAG CTG GCA GAG GGA AAG GCA CTG GGT ACC TCA GGG TGA GCA GAG GGC ACT 1359             1368             1377             1386             1395             1404
GGG CTG GGG CAC AGC CCC TGC TTC CCT GCA CCC CAT TCC CAC CCT GAA GTT CTG 1413             1422             1431             1440             1449             1458
CAC CTG CAC CTT TGT TGA ATT GTG GTA GCT TAG GAG GAT GTC GGG GTT GAA GGG 1467             1476             1485             1494             1503             1512
TGG TAT CTT GGC AGT TGA AGC TGG GGC AAG AAC TCT GGG CTT GGG TAA TGA AGC
```

FIGURE 1D

```
      1521            1530            1539           1548          1557         1566
AGG AAG AAA ATT TTC TTG ATC TTA AGC CCA CCT CTG TTC TGC CCC CCG CTT TTC 1575            1584            1593           1602          1611         1620
CTC TGT TTG AAT ACT ATA AAT TTT CTG GTT CCC TTT GGA TTT ATG GAT AAG TGT 1629            1638
CCC CCT CCA TGT TCC AGG AAA   3'
```

FIGURE 1E

```
  1  MVCRLPVSKKTLLCSFQVLDELGRHVLLRKDCGPVDTKVP  concensus
  1  M--------------------------------------  GI 555662

41  GAVEPKSAFTQGSAMISSLSQNHPDNRNETFSXISLLNE   concensus
  2  -------------------------------PVNL----  GI 555662

81  DPLSQDLPVKMASIFKNFVITYNRTYESKEEARWRLSVFV  concensus
  6  EYLGFKLPGNVDEKYVQFKLKYRKQYHETEDEI-RFNIFK  GI 555662

121  NNMVRAQKIQALDRGTAQYGVTKFSDLTEEFRTIYLNTL   concensus
 45  SNILKAQLYQVFVRGSAIYGVTPYSDLTTDEFARTHLTAS  GI 555662

161  LRKEPGNKMKQAKSVG--DLAPPEWDWRSKGAVTKVKDQ   concensus
 85  -WVPSSRSNTPTSLGKEVNNIPKNFDWREKGAVTEVKNQ   GI 555662

198  GMCGSCWAFSVTGNVEGQWFLNQGTLLSLSEQELLDCDKM  concensus
124  GMCGSCWAFSTTGNVESQWFRKTGKLLSLSEQQLVDCDGL  GI 555662

238  DKACMGGLPSNAYSAIKNLGGLETEDDYSYQGHMQSCNFS  concensus
164  DDGCNGGLPSNAYESIIKMGGLMLEDNYPYDAKNEKCHLK  GI 555662

278  AEKAKVYINDSVELSQNEQKLAAWLAERGPISVAINAFGM  concensus
204  TDGVAVYINSSVNLTQDETELAAWLYHNSTISVGMNALLL  GI 555662
```

FIGURE 2A

```
318 Q F Y R H G I S R P L R P L C S P W L I D H A V L L V G Y G - N R S D V P F W A   concensus
244 Q F Y Q H G I S H P W W I F C S K Y L L D H A V L L V G Y G V S E K N E P F W I   GI 555662

357 I K N S W G T D W G E K G Y Y Y L H R G S G A C G V N T M A S S A V V D          concensus
284 V K N S W G V E W G E N G Y F R M Y R G D G S C G I N T V A T S A M I Y          GI 555662
```

```
5' CAC GCG TCC GCA GCG ATG TCT CCA CCG CTG CAA CCC CTG CTG CTG CCT CTT CTG
               9              18              27              36              45              54
               -   -   -      -   -   M       S   P   P       L   Q   P       L   L   L       P   L   L

CTG CCT CTG CTG AAT GTG GAG CCT TCC GGG GCC ACA CTG AAC ATC CGC ATC CCT CTT
              63              72              81              90              99             108
   L   P   L   L   N   V      E   P   S       G   A   T       L   N   I       R   I   P   L

CAT CGA CAA CCT GGA CGC AGG ATC CTG AAC CTA CTG AGG GGA TGG AGA GAA
              117             126             135             144             153             162
   H   R   Q   P   G   R      R   I   L       N   L   L       R   G   W       R   E

CCA GCA GAG CTC CCC AAG TTG GGG GCC CCA TCC CCT GGG GAC AAG CCC ATC TTC
              171             180             189             198             207             216
   P   A   E   L   P   K      L   G   A       P   S   P       G   D   K       P   I   F

GTA CCT CTC TCG AAC TAC AGG GAT GTG CAG TAT TTT GGG GAA ATT GGG CTG GGA
              225             234             243             252             261             270
   V   P   L   S   N   Y      R   D   V   Q   Y   F       G   E   I       G   L   G

ACG CCT CCA CAA AAC TTC GCC TTT GAC ACT GTT GGC TCC AAT CTC TGG
              279             288             297             306             315             324
   T   P   P   Q   N   F      A   F   D   T   V   G       S   N   L   W

GTC CCG TCC AGG AGA TGC CAC TTC AGT GTG CCC TGC TGG TTA CAC CAC CGA
              333             342             351             360             369             378
   V   P   S   R   R   C      H   F   S   V   P   C       W   L   H   H   R
```

```
         387          396          405          414          423          432
TTT GAT CCC AAA GCC TCT AGC TCC TTC CAG GCC AAT GGG ACC AAG TTT GCC ATT
 F   D   P   K   A   S   S   S   F   Q   A   N   G   T   K   F   A   I 441          450          459          468          477          486
CAA TAT GGA ACT GGG CGG GTA GAT GGA ATC CTG AGC GAG GAC AAG CTG ACT ATT
 Q   Y   G   T   G   R   V   D   G   I   L   S   E   D   K   L   T   I 495          504          513          522          531          540
GGT GGA ATC AAG GGT GCA TCA GTG ATT TTC GGG GAG GCT CTC TGG GAG CCC AGC
 G   G   I   K   G   A   S   V   I   F   G   E   A   L   W   E   P   S 549          558          567          576          585          594
CTG GTC TTC GCT TTT GCC CAT TTT GAT GGG ATA TTG GGC CTC GGT TTT CCC ATT
 L   V   F   A   F   A   H   F   D   G   I   L   G   L   G   F   P   I 603          612          621          630          639          648
CTG TCT GTG GAA GGA GTT CGG CCC CCG ATG GAT GTA CTG GTG GAG CAG GGG CTA
 L   S   V   E   G   V   R   P   P   M   D   V   L   V   E   Q   G   L 657          666          675          684          693          702
TTG GAT AAG CCT GTC TTC TCC TTT TAC CTC AAC AGG GAC CCT GAA GAG CCT GAT
 L   D   K   P   V   F   S   F   Y   L   N   R   D   P   E   E   P   D 711          720          729          738          747          756
GGA GAG CTG CTG GTC CTG GGG GGC TCG GAC CCG GCA CAC TAC ATC CCA CCC CTC
 G   E   L   L   V   L   G   G   S   D   P   A   H   Y   I   P   P   L
```

FIGURE 5B

```
              765      774      783      792      801      810
      ACC TTC GTG CCA GTC CCC TAC TGG CAC ATG GAG CGT GTG
       T   F   V   P   V   P   Y   W   H   M   E   R   V 819      828      837      846      855      864
      AAG GTG GGC CCA GGG CTG ACT CTC TGT GCC AAG GGC TGT GCT GAT
       K   V   G   P   G   L   T   L   C   A   K   G   C   A   D 873      882      891      900      909      918
      ACG GGC ACG TCC CTC ATC ACA GGA CCC ACT GAG ATC CGG GCC CTG CAT GCA
       T   G   T   S   L   I   T   G   P   T   E   I   R   A   L   H   A 927      936      945      954      963      972
      GCC ATT GGG GGA ATC CCC TTG CTG GCT GGG GAG TAC ATC ATC CTG TGC TCG GAA
       A   I   G   G   I   P   L   L   A   G   E   Y   I   I   L   C   S   E 981      990      999      1008     1017     1026
      ATC CCA AAG CTC CCC GCA GTC TCC TTC CTT CTT GGG GTC TGG TTT AAC CTC
       I   P   K   L   P   A   V   S   F   L   L   G   V   W   F   N   L 1035     1044     1053     1062     1071     1080
      ACG GCC CAT GAT TAC GTC ATC CAG ACT ACT CGA AAT GAC GTC TTC TTG GGG ACG
       T   A   H   D   Y   V   I   Q   T   T   R   N   D   V   F   L   G   T 1089     1098     1107     1116     1125     1134
      TAT GTG GCC GTC TTC GAC CGC GGG GAC ATG AAG AGC AGC GCC CGG GTG GGC CTG
       Y   V   A   V   F   D   R   G   D   M   K   S   S   A   R   V   G   L
```

FIGURE 5C

```
          1143                1152                1161                1170                1179           1188
GCG CGC GCT CGC ACT CGC GGA GCG GAC CTC GGA TGG GGA GAG ACT GCG CAG GCG
 A   R   A   R   T   R   G   A   D   L   G   W   G   E   T   A   Q   A 1197                1206                1215                1224                1233           1242
CAG TTC CCC GGG TGA CGC CCA AGT GAA GCG CAT GCG CAG CGG GTG GTC GCG GAG
 Q   F   P   G   *

1251                1260                1269                1278                1287           1296
GTC CTG CTA CCC AGT AAA AAT CCA CTA TTT CCA TTG AAA AAA AAA AAA AAA AAA

```
  1  M S P P P L L Q P L L L L P L L N V E P S G A T L I R I P L H R V Q P G R R I   clone312099
  1  M Q E S S L - - - L P L A L C L L A - - A P A S A L V R I P L H K F T S I R R T   GI 181180

41  L N L L R G W - - - - R E P A E L P K L G A P S P G D K P I F V P L S N Y R       clone312099
 36  M S E V G G S V E D L I A K G P V S K Y S Q A V P A V T E G P I P E V L K N Y M   GI 181180

75  D V Q Y F G E I G L G T P P Q N F T V A F D T G S S N L W V P S R R C H F F S V   clone312099
 76  D A Q Y Y G E I G I G T P P Q C F T V F D T G S S N L W V P S I H C K L L D I     GI 181180

115  P C W L H H R F D P K A S S F Q A N G T K F A I Q Y G T G R V D G I L S E D K     clone312099
116  A C W I H H K Y N S D K S S T Y V K N G T S F D I H Y G S G S L S G Y L S Q D T   GI 181180

155  L T I - - - - - - - - - - - - - G G I K G A S V I F G E A L W E P S L V F A F A H F   clone312099
156  V S V P C Q S A S S A S A L G G V K V E R Q V F G E A T K Q P G I T F I A A K E   GI 181180

184  D G I L G L G F P I L S V E G V R P P M D V L V E Q G L L D K P V F S F Y L N R   clone312099
196  D G I L G M A Y P R I S V N N V L P V F D N L M Q Q K L V D Q N I F S F Y L S R   GI 181180

224  D P E E P D G G E L V L G G S D P A H Y I P P L T F V P V T V P A Y W Q I H M E   clone312099
236  D P D A Q P G G E L M L G G T D S K Y Y K G S L S Y L N V T R K A Y W Q V H L D   GI 181180

264  R V K V G P G L T L C A K G C A A I L D T G T S L I T G P T E E I R A L H A A I   clone312099
276  Q V E V A S G L T L C K E G C E A I V D T G T S L M V G P V D E V R E L Q K A I   GI 181180
```

FIGURE 6A

```
304 G G I P L L A G E Y I I L C S E I P K L P A V S F L L G G V W F N L T A H D Y V   clone312099
316 G A V P L I Q G E Y M I P C E K V S T L P A I T L K L G G K G Y K L S P E D Y T   GI 181180

344 I Q T T R N - - - - - - - - - - - - - - - - - - D V F L G T Y V A   clone312099
356 L K V S Q A G K T L C L S G F M G M D I P P P S G P L W I L G D V F I G R Y Y T   GI 181180

359 V F D R G D M K S S A R V G L A R A R T R G A D L G W G E T A Q A Q F P G   clone312099
396 V F D R D N - - - N R V G F A E A - - - A R L                                     GI 181180
```

FIGURE 6B

TWO NOVEL HUMAN CATHESPIN PROTEINS

This application is a divisional application of U.S. application Ser. No. 08/723,938, filed Sep. 26, 1996, now U.S. Pat. No. 5,776,759.

FIELD OF THE INVENTION

The present invention relates to nucleic acid and amino acid sequences of two novel human cathepsin proteins and to the use of these sequences in the diagnosis, study, prevention and treatment of disease.

BACKGROUND OF THE INVENTION

The cathepsin family of lysosomal protease includes the cysteine protease; cathepsins B, H, K, L, O2, and S, and the aspartyl protease; cathepsins D, and G. The various members of this endosomal protease family are differentially expressed. Some, such as cathepsin D, have a ubiquitous tissue distribution while others, such as cathepsin L, are found only in monocytes, macrophages, and other cells of the immune system.

The cathepsins represent the major endopeptidases in the lysosome (Huisman W, et al. (1974) Biochem Biophys Acta 370:297–307) and as such participate in the degradation of proteins entering the vacuolar system by endocytosis and in the turnover of cytoplasmic proteins. The cathepsins are also active in 1) initiation of proteolytic cascades by proenzyme activation, 2) processing of the II alpha beta heterodimer in endosomes for expression of functional MHC class II molecules which bind antigenic peptides, and 3) processing of antigen in antigen-presenting cells. The secreted forms of several members of this family function in tissue remodeling through degradation of collegen, laminin, elastin, and other structural proteins of basement membranes (Mizuochi T, (1994) Immunol Lett 43:189–193, Baldwin E T, (1993) Proc Natl Acad Sci 90:6796–6800). Both cysteine and aspartyl cathepsins are used by various parasitic protozoa for the catabolism of host cell proteins and/or facilitating host invasion (Becker M M et al. (1995) J Biol Chem 270: 24496–24501, Rosenthal P J et al. (1988) J Clin Invest 82:1560–1566, McKerrow J H (1993) Annu Rev Micrbiol 47:821–853).

The various cathepsin proteases differ in their gene structures and in their transcriptional regulation. The cathepsin D gene promoter has a compound structure with features of both housekeeping genes (high G+C content and potential transcription factor SP-1 sites) and regulated genes (TATA sequence). RNase protection assays show that transcription is initiated at five major transcription sites (transcription site-I to transcription site-V) spanning 52 base pairs. Site-directed mutagenesis studies indicate that the TATA box is essential for initiation of cathepsin D gene transcription at transcription site-I. This suggests that cathepsin D behaves, depending on the conditions, as a housekeeping gene with multiple start sites or as a hormone-regulated gene that can be controlled from its TATA box (Cavailles V (1993) Proc Natl Acad Sci 90:203–207). The cathepsin L gene promoter has no TATA box but includes several SP-1 sites, two AP-2 transcription regulatory element binding sites (a promoter under the control of the tumor promoter and cAMP), and a cAMP response element. Experimental data confirm that the expression of cathepsin L is induced by malignant transformation, growth factors, tumor promoters, and cyclic AMP (Troen B et al.(1991) Cell Growth Differ 2:23–31).

Altered regulation and expression of these two different cathepsins is evident in disease states. Cathepsin D is overproduced and hypersecreted by breast cancer cells. Clinical studies show a strong correlation between high concentrations of cathepsin D in the cytosol of primary tumor cells and further occurrence of metastasis. Cathepsin D is expressed at high levels in hormone independent breast cancer, is induced by estrogen in hormone dependent breast cancer, and appears to be independent of other more classical prognostic factors. In nude mice, transfection of cathepsin D cDNA into tumor cells increases their metastatic potential, suggesting that overexpression of this protease may be one of the factors responsible for metastasis (Rochefort H (1992) Acta Oncol 31:125–30, Long B J (1996) Cancer Lett 99:233–238). The mechanism by which this protease might facilitate metastasis is not fully characterized, although cathepsin D has the potential to initiate a proteolytic cascade, to degrade extracellular matrix and to liberate growth factors from the matrix. In vitro studies have noted that transfected cathepsin D stimulates high density cancer cell growth via an intracellular mechanism leading to a decreased secretion of growth inhibitors (Liaudet E (1995) Cell Growth Differ 6:1045–1052). Altered cathepsin D levels are present in biopsy specimens in prostate and bladder carcinomas and are shown to correlate with tumor grade (Ross J S (1995) Am J Clin Pathol 104:36–41, Dickinson A J (1995) J Urol 154:237–241).

Altered cathepsin activity and/or distribution may play a role in certain brain diseases. In Alzheimer's disease, A4 amyloid peptide, the main constituent of amyloid plaques and cerebrovascular amyloid deposits, derives from a large amyloid precursor protein (APP) by the action of endoproteases which release the amino and carboxyl termini to generate the aggregating form of A4. In the brains of Alzheimer's patients, more than 90% of the pyramidal neurons in lamina V and 70% in lamina III displayed 2- to 5-fold elevated levels of cathepsin D mRNA by in situ hybridization compared with neurologically normal controls. An endogenous protease activity from diseased samples was found to be active in acidic conditions and inhibited by pepstatin, two characteristics of cathepsin D, suggesting that a cathepsin D-like activity from human brain may be responsible for APP processing (Evin G (1995) Biochemistry 34:14185–14192, Cataldo A M (1995) Neuron 14:671–680). There is a significant increase in cathepsin D activity in biopsies from Huntington's disease (Mantle D (1995) J Neurol Sci 131:65–70) and there are increased levels of cathepsin D mRNA in scrapie-infected mice (Diedrich J F (1991) J Virol 65:4759–4768).

Abnormal regulation of cathepsins is observed in several inflammatory disease states. In fibroblastoid synovial lining cells isolated from rheumatoid and other chronic inflammatory synovial tissues, the mRNA for stromelysin, vimentin, IL-4, IL-6, TIMP-1, cathepsin D, gelatinase, TGF alpha, c-fms and DR beta is preferentially expressed. This modulated pattern of gene expression is correlated with the phenotype of this inflammatory condition (Ritchlin C et al. (1994) Scand J Immunol 40:292–298). Cathepsin L and D expression was evaluated in synovial tissues from patients with rheumatoid arthritis (RA) and osteoarthritis (OA), using in situ hybridization with digoxigenin-labeled RNA probes. Both RA and OA synovial tissue expressed cathepsins L and D. The expression of the cathepsins was markedly higher in interstitial regions and in perivascular infiltrates of RA synovial tissue compared with OA specimens. The differential expression of cathepsins L and D mRNA in RA and OA synovial tissues supports the concept that these enzymes may contribute to the influx of mononuclear cells into the synovium and suggests that the adhesion of synovial cells to cartilage mediates the invasive/destructive process in RA (Keyszer G M (1995) Arthritis Rheum 38:976–984.

The cathepsins are believed to be involved in several other diseases states. In an experimental model of human glomerular disease, the administration of a specific, irreversible inhibitor of cysteine protease (trans-epoxysuccinyl-L-leucylamido-3-methyl-butane) significantly reduces proteinuria in rats (Baricos W H (1991) Arch Biochem Biophys 288:468–72.) The fibroblasts from patients with mucolipidosis II and III have a severely compromised capacity for endogenous lysosomal protein degradation that appears to result from multiple cathepsin deficiencies (Kopitz J (1993) Biochem J 295 (Pt 2): 577–580). The platelet aggregating cysteine protease implicated in thrombotic thrombocytopenic purpura shows the characteristics of a lysosomal cathepsin (Consonni R (1994) Br J Haematol 87:321–324).

Cathepsin D knockout mice develop normally during the first 2 weeks, stop thriving in the third week and die in a state of anorexia at day 26±1. An atrophy of the ileal mucosa observed in the third week progresses towards widespread intestinal necroses accompanied by thromboemboli. The thymus and spleen undergo massive destruction with loss of T and B cells. The lysosomal bulk proteolysis is, however, maintained. These results suggest that the major functions of cathepsin D involve limited proteolysis of proteins regulating cell growth and/or tissue homeostasis (Saftig P, (1995) EMBO J 14:3599–3608).

Cathepsins have a role in processes that involve proteolysis of specific proteins and tissues in local microenvironments including inflammation, metastasis and peptide and proenzyme processing. The increased expression and differential regulation of these protease is linked to the metastatic potential of a variety of cancers and as such is of therapeutic and prognostic interest. Evidence of the involvement of cathepsins associated with protein processing in diseases such as Alzheimer's disease, Huntington's disease, mucolipidosis and arthritic inflammation suggests that modulation of the cathepsins may ameliorate these disease processes. The polynucleotide sequences and proteins of the claimed invention would satisfy this need by providing the means for diagnosis, study, prevention and treatment of these diseases.

SUMMARY OF THE INVENTION

The present invention discloses two novel human cathepsin proteins, hereinafter referred to as HCP-1 and HCP-2 and, collectively, HCPs, which share features with other proteins involved in proteolysis. Accordingly, the invention features substantially purified HCP-1 and HCP-2, as shown in the amino acid sequence of SEQ ID NO:1 and SEQ ID NO:5.

One aspect of the invention features isolated and substantially purified polynucleotides which encode HCPs. In a particular aspect, the polynucleotides are the nucleotide sequences of SEQ ID NO:1 and SEQ ID NO:5. In addition, the invention features polynucleotide sequences that hybridize under stringent conditions to SEQ ID NO:1 and SEQ ID NO:5.

The invention further relates to the nucleic acid sequence encoding HCP, oligonucleotides, peptide nucleic acids (PNA), fragments, portions or antisense molecules thereof. The present invention also relates, in part, to the inclusion of the nucleic acid sequence encoding HCP in an expression vector which can be used to transform host cells.

The present invention also relates to a method for producing HCP or a fragment thereof. It contemplates the delivery of purified HCP, alone or in a pharmaceutically acceptable excipient, to cancerous cells or tissues. It also encompasses antibodies which bind specifically to HCP and can be used to monitor testing of cathepsin-expressing tissues.

BRIEF DESCRIPTION OF THE FIGURES

FIG. 1 shows the amino acid sequence (SEQ ID NO:1) and nucleic acid sequence (SEQ ID NO:2) for HCP-1.

FIG. 2 shows the amino acid alignment of HCP-1 and GI 555662 (Smith A M, (1994) Mol Biochem Parasitol 67 (1):11–19) The alignment was produced using the multisequence alignment program of DNAStar™ software (DNAStar Inc, Madison Wis.).

FIG. 5 shows the amino acid sequence (SEQ ID NO:3) and nucleic acid sequence (SEQ ID NO:4) for HCP-2.

FIG. 6 shows the amino acid alignment of HCP-2 and GI 181180 (Faust P L (1985) Proc Natl Acad Sci 82 (15) 4910–4914). (DNAStar Inc, Madison Wis.).

DESCRIPTION OF THE INVENTION

Definitions

Figure 3:
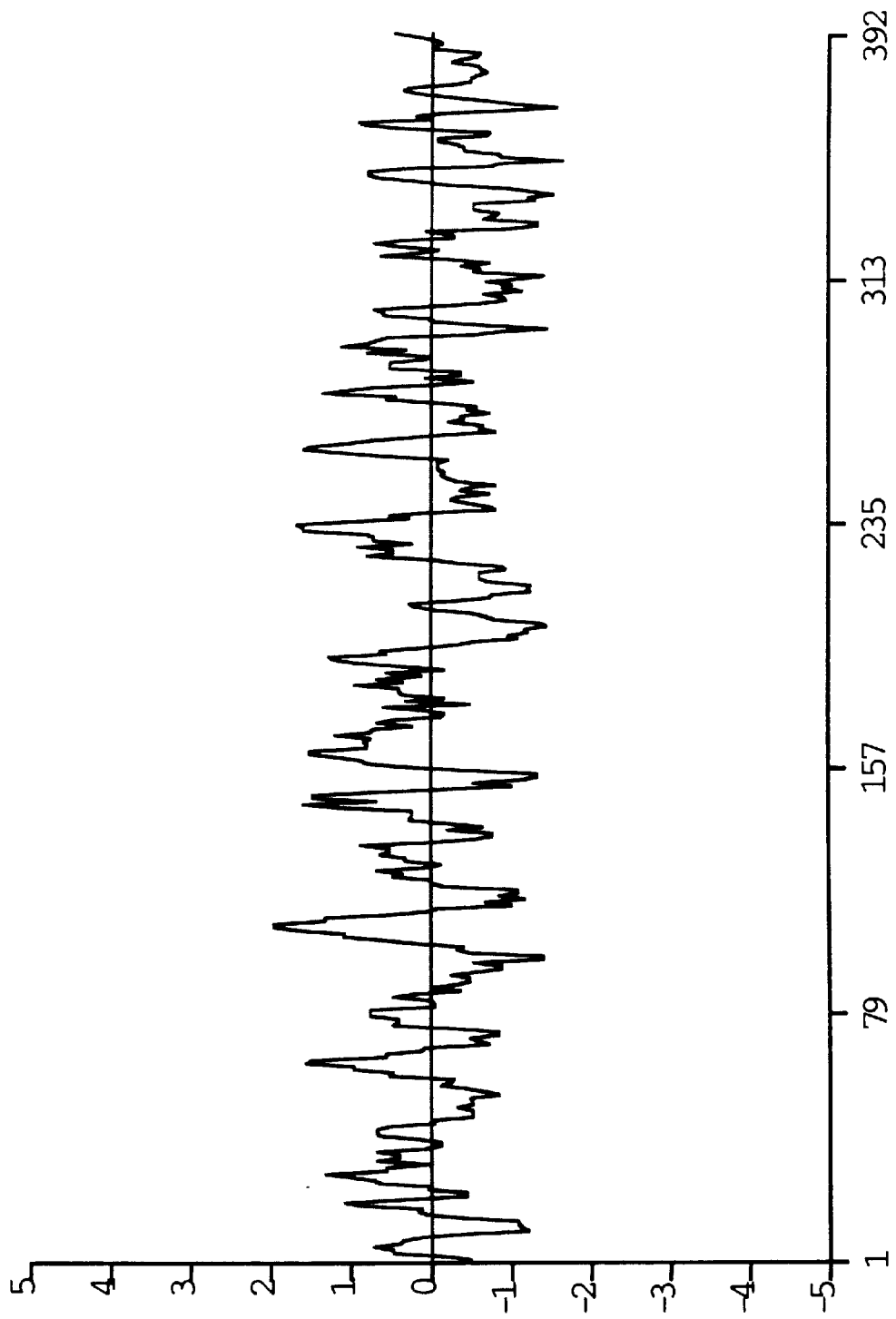
FIG. 3 shows the hydrophobicity plot for HCP-1; the X axis reflects amino acid position, and the negative Y axis, hydrophobicity (MacDNAsis software, Hitachi Software Engineering Co Ltd, San Bruno Calif.).

"Nucleic acid sequence" as used herein refers to an oligonucleotide, nucleotide or polynucleotide, and fragments or portions thereof, and to DNA or RNA of genomic or synthetic origin which may be single- or double-stranded, and represent the sense or antisense strand. Similarly, amino acid sequence as used herein refers to peptide or protein sequence.

"Consensus" as used herein may refer to a nucleic acid sequence 1) which has been resequenced to resolve uncalled bases, 2) which has been extended using XL-PCR (Perkin Elmer) in the 5' or the 3' direction and resequenced, 3) which has been assembled from the overlapping sequences of more than one Incyte clone GCG Fragment Assembly System, (GCG, Madison Wis.), or 4) which has been both extended and assembled.

"Peptide nucleic acid" as used herein refers to a molecule which comprises an oligomer to which an amino acid residue, such as lysine, and an amino group have been added. These small molecules, also designated anti-gene agents, stop transcript elongation by binding to their complementary (template) strand of nucleic acid (Nielsen P E et al (1993) Anticancer Drug Des 8:53–63).

A "deletion" is defined as a change in either nucleotide or amino acid sequence in which one or more nucleotides or amino acid residues, respectively, are absent.

An "insertion" or "addition" is that change in a nucleotide or amino acid sequence which has resulted in the addition of one or more nucleotides or amino acid residues, respectively, as compared to the naturally occurring HCP.

A "substitution" results from the replacement of one or more nucleotides or amino acids by different nucleotides or amino acids, respectively.

As used herein, HCP refers to the amino acid sequence of substantially purified HCP obtained from any species, particularly mammalian, including bovine, ovine, porcine, murine, equine, and preferably human, from any source whether natural, synthetic, semi-synthetic or recombinant.

A "variant" of HCP is defined as an amino acid sequence which differs by one or more amino acids. The variant may have "conservative" changes, wherein a substituted amino acid has similar structural or chemical properties, eg, replacement of leucine with isoleucine. More rarely, a variant may have "nonconservative" changes, eg, replacement of a glycine with a tryptophan. Similar minor variations may also include amino acid deletions or insertions, or both. Guidance in determining which and how many amino acid residues may be substituted, inserted or deleted without abolishing biological or immunological activity may be found using computer programs well known in the art, for example, DNAStar software.

The term "biologically active" refers to an HCP having structural, regulatory or biochemical functions of naturally occurring HCP. Likewise, "immunologically active" defines the capability of the natural, recombinant or synthetic HCP, or any oligopeptide thereof, to induce a specific immune response in appropriate animals or cells and to bind with specific antibodies.

The term "derivative" as used herein refers to the chemical modification of nucleic acids encoding HCP or the encoded HCP. Illustrative of such modifications would be replacement of hydrogen by an alkyl, acyl, or amino group. A nucleic acid derivative would encode a polypeptide which retains essential biological characteristics of natural HCP.

As used herein, the term "substantially purified" refers to molecules, either nucleic or amino acid sequences, that are removed from their natural environment, isolated or separated, and are at least 60% free, preferably 75% free, and most preferably 90% free from other components with which they are naturally associated.

The term "hybridization" as used herein shall include "any process by which a strand of nucleic acid joins with a complementary strand through base pairing" (Coombs J (1994) *Dictionary of Biotechnology*, Stockton Press, New York N.Y.). Amplification is defined as the production of additional copies of a nucleic acid sequence and is generally carried out using polymerase chain reaction technologies well known in the art (Dieffenbach C W and G S Dveksler (1995) *PCR Primer, a Laboratory Manual*, Cold Spring Harbor Press, Plainview N.Y.).

"Stringency" typically occurs in a range from about Tm-5° C. (5° C. below the Tm of the probe)to about 20° C. to 25° C. below Tm. As will be understood by those of skill in the art, a stringency hybridization can be used to identify or detect identical polynucleotide sequences or to identify or detect similar or related polynucleotide sequences.

Preferred Embodiments

Figure 4:
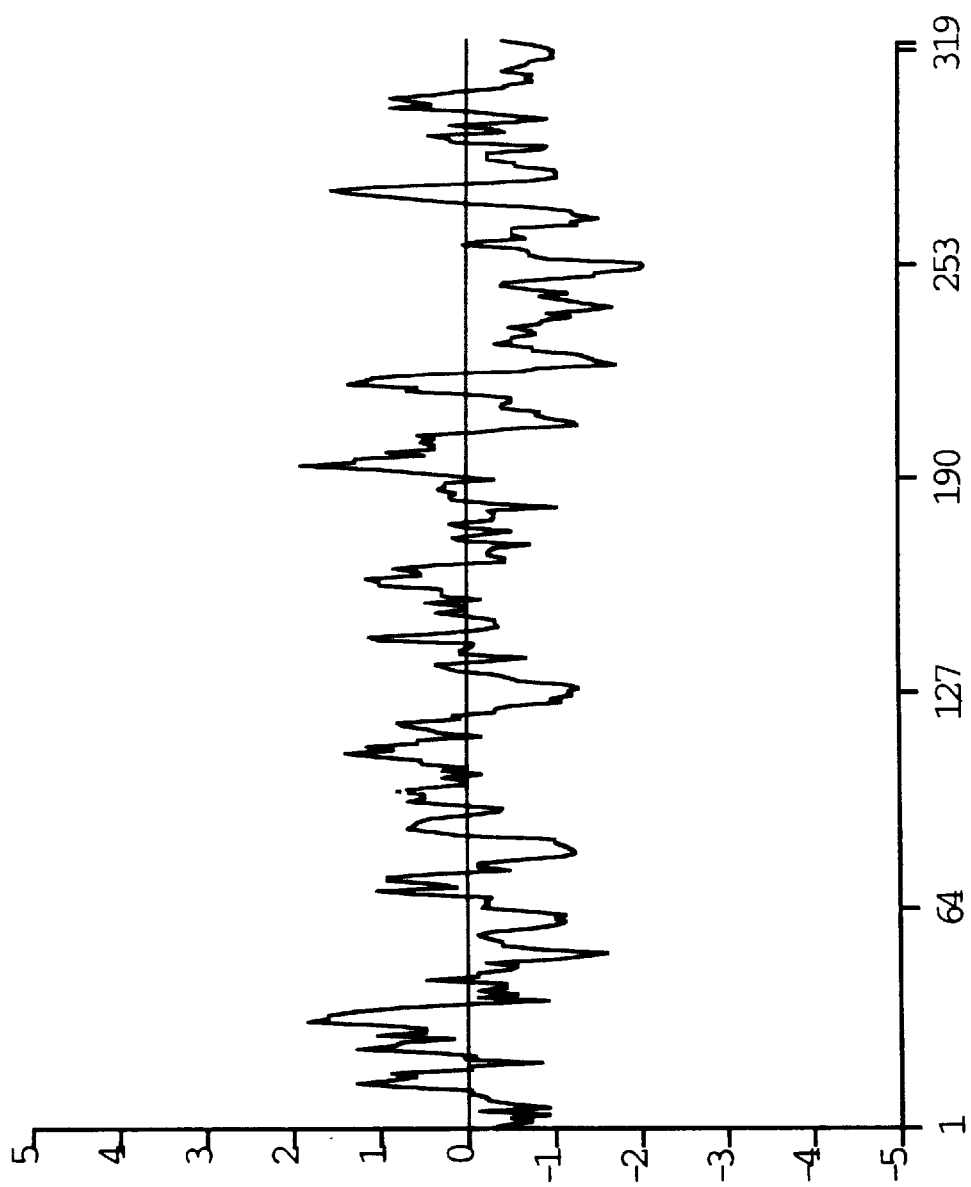
FIG. 4 shows the hydrophobicity plot for GI 555662 (MacDNAsis software).

The consensus nucleotide sequence for HCP-1 (SEQ ID NO:1), disclosed herein, encodes a novel human cathepsin protein of 392 amino acid residues. The consensus sequence is based on the extension and assembly of the following Incyte clones: 152940 (FIBRAGT02), 398290 (PITUNOT02), 723324 (SYNOOAT01), 787555 (PROSNOT05), and 937823 (CERVNOT01). HCP-1 has 392 amino acid residues including seven conserved cysteines In addition, HCP-1 has 49% identity to Schistosoma mansoni puerto rican preprocathepsin L (GI 555662, FIG. 2) as well as similarities in hydrophobicity (FIGS. 4 and 5). The amino acid alignments of the consensus sequence and GI 555662 are shown in FIG. 2. Using the numbers for the consensus sequence at the side of the figure as a reference, the following cysteine residues are conserved: $C_{200}$, $C_{203}$, $C_{234}$, $C_{241}$, $C_{274}$, $C_{332}$, and $C_{380}$, The hydrophobicity plot for the consensus sequence aligns with that for GI 555662 further suggesting similar functions as a cysteine protease.

Figure 7:
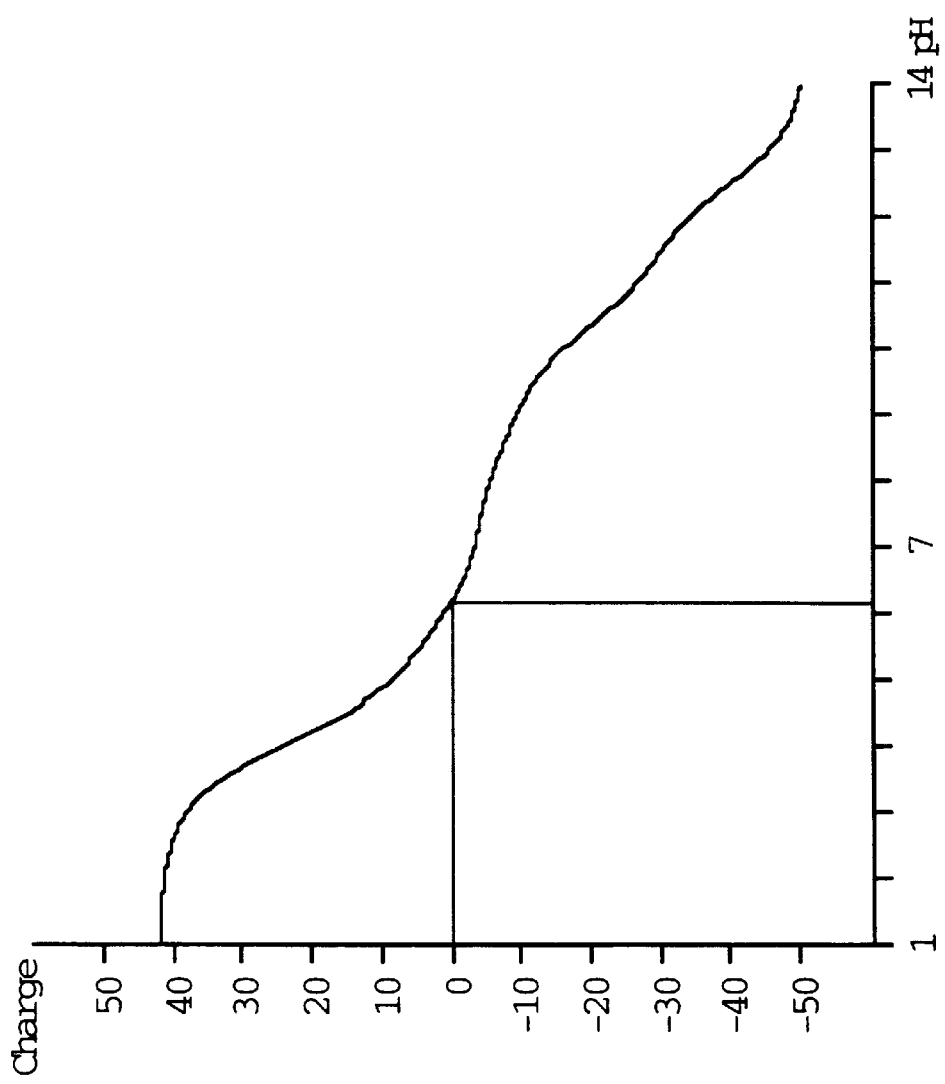
FIG. 7 shows the isoelectric plot for HCP-2 (MacDNAsis software).
Figure 8:
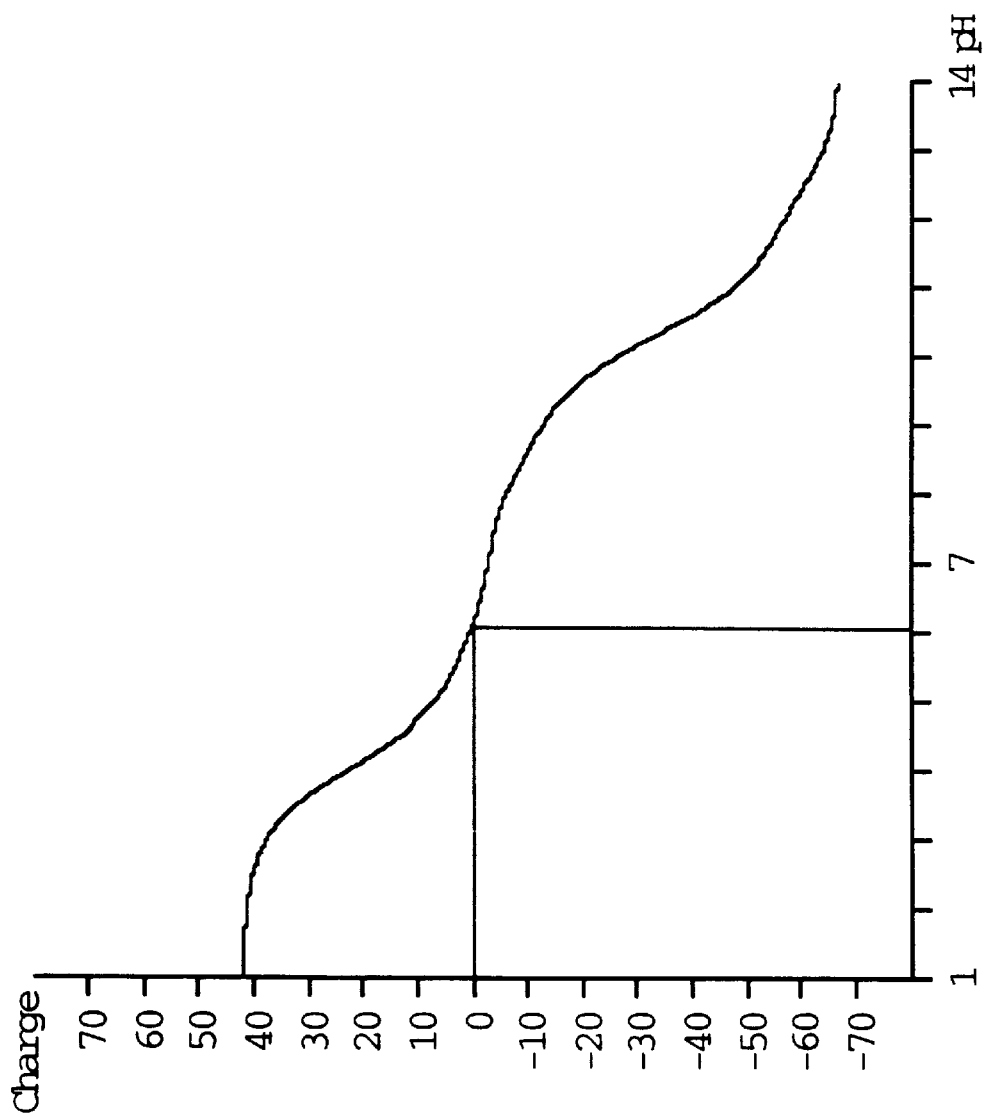
FIG. 8 shows the isoelectric plot for GI 181180 (MacDNAsis software).

The Incyte clone number 312099, HCP-2, encodes a novel human cathepsin protein of 395 amino acid residues (FIG. 5). The clone sequence is based on the extension of Incyte clone number 312099 (LUNGNOT02). HCP-2 has 395 amino acid residues including nine conserved aspartic acids, $D_{96}$, $D_{153}$, $D_{184}$, $D_{213}$, $D_{224}$, $D_{239}$, $D_{283}$, $D_{350}$, and $D_{361}$ and four conserved cysteines, $C_{109}$, $C_{116}$, $C_{274}$, and $C_{317}$. HCP-2 has 43% identity with human preprocathepsin D (GI 181180, FIG. 6) and a similar isoelectric point (FIGS. 7 and 8).

The HCP Coding Sequences

The nucleic acid and deduced amino acid sequences of the HCP-1 is shown in FIG. 1. In accordance with the invention, any nucleic acid sequence which encodes the HCP can be used to generate recombinant molecules which express HCP. In a specific embodiment described herein, a partial sequence encoding HCP-1 was first isolated as Incyte Clone 152940 from an ataxia telangiectasia fibroblast cDNA library (FIBRAGT02).

The nucleic acid and deduced amino acid sequences of the HCP-2 is shown in FIG. 5. In accordance with the invention, any nucleic acid sequence which encodes the HCP can be used to generate recombinant molecules which express HCP. In a specific embodiment described herein, a partial sequence encoding HCP-2 was first isolated as Incyte Clone 312099 from a cDNA library (LUNGNOT02).

It will be appreciated by those skilled in the art that as a result of the degeneracy of the genetic code, a multitude of HCP-encoding nucleotide sequences, some bearing minimal homology to the nucleotide sequences of any known and naturally occurring gene may be produced. The invention contemplates each and every possible variation of nucleotide sequence that could be made by selecting combinations based on possible codon choices. These combinations are made in accordance with the standard triplet genetic code as applied to the nucleotide sequence encoding naturally occurring HCP, and all such variations are to be considered as being specifically disclosed.

Although nucleotide sequences which encode HCP and their variants are preferably capable of hybridizing to the nucleotide sequence of the naturally occurring sequences under appropriately selected conditions of stringency, it may be advantageous to produce nucleotide sequences encoding HCP or their derivatives possessing a substantially different codon usage. Codons may be selected to increase the rate at which expression of the peptide occurs in a particular prokaryotic or eukaryotic expression host in accordance with the frequency with which particular codons are utilized by the host. Other reasons for substantially altering the nucleotide sequence encoding HCP and their derivatives without altering the encoded amino acid sequences include the production of RNA transcripts having more desirable properties, such as a greater half-life, than transcripts produced from the naturally occurring sequence.

A DNA sequence, or portions thereof, encoding HCP and their derivatives may be produced entirely by synthetic chemistry, after which the synthetic gene may be inserted into any of the many available DNA vectors and cell systems using reagents that are generally available. Moreover, synthetic chemistry may be used to introduce mutations into a sequence encoding HCP or any portion thereof.

Also included within the scope of the present invention are polynucleotide sequences that are capable of hybridizing to the nucleotide sequences of SEQ ID NO:2 and SEQ ID NO:4 under various conditions of stringency. Hybridization conditions are based on the melting temperature (Tm) of the nucleic acid binding complex or probe, as taught in Berger and Kimmel (1987, *Guide to Molecular Cloning Techniques, Methods in Enzymology*, Vol 152, Academic Press, San Diego Calif.) incorporated herein by reference, and may be used at a defined "stringency".

Altered nucleic acid sequences encoding HCP which may be used in accordance with the invention include deletions, insertions or substitutions of different nucleotides resulting in a polynucleotide that encodes the same or a functionally equivalent HCP. The protein may also show deletions, insertions or substitutions of amino acid residues which produce a silent change and result in functionally equivalent HCP. Deliberate amino acid substitutions may be made on the basis of similarity in polarity, charge, solubility, hydrophobicity, hydrophilicity, and/or the amphipathic nature of the residues as long as the biological activity of HCP is retained. For example, negatively charged amino acids include aspartic acid and glutamic acid; positively charged amino acids include lysine and arginine; and amino acids with uncharged polar head groups having similar hydrophilicity values include leucine, isoleucine, valine; glycine, alanine; asparagine, glutamine; serine, threonine phenylalanine, and tyrosine.

Included within the scope of the present invention are alleles encoding HCP. As used herein, an "allele" or "allelic sequence" is an alternative form of the nucleic acid sequence encoding HCP. Alleles result from a mutation, ie, a change in the nucleic acid sequence, and generally produce altered mRNAs or polypeptides whose structure or function may or may not be altered. Any given gene may have none, one or many allelic forms. Common mutational changes which give rise to alleles are generally ascribed to natural deletions, additions or substitutions of amino acids. Each of these types of changes may occur alone, or in combination with the others, one or more times in a given sequence.

Methods for DNA sequencing may be used which are well known in the art and employ such enzymes as the Klenow fragment of DNA polymerase I, Sequenase® (U.S. Biochemical Corp, Cleveland Ohio)), Taq polymerase (Perkin Elmer, Norwalk Conn.), thermostable T7 polymerase (Amersham, Chicago Ill.), or combinations of recombinant polymerases and proofreading exonucleases such as the ELONGASE Amplification System marketed by Gibco BRL (Gaithersburg Md.). Preferably, the process is automated with machines such as the Hamilton Micro Lab 2200 (Hamilton, Reno Nev.), Peltier Thermal Cycler (PTC200; MJ Research, Watertown Mass.) and the ABI 377 DNA sequencers (Perkin Elmer).

Extending the Polynucleotide Sequence

The polynucleotide sequences encoding HCP may be extended utilizing partial nucleotide sequence and various methods known in the art to detect upstream sequences such as promoters and regulatory elements. For example, the method of Gobinda et al (1993; PCR Methods Applic 2:318–22) involves "restriction-site" polymerase chain reaction (PCR) as a direct method which uses universal primers to retrieve unknown sequence adjacent to a known locus. First, genomic DNA is amplified in the presence of primer to a linker sequence and a primer specific to the known region. The amplified sequences are subjected to a second round of PCR with the same linker primer and another specific primer internal to the first one. Products of each round of PCR are transcribed with an appropriate RNA polymerase and sequenced using reverse transcriptase.

Inverse PCR can be used to amplify or extend sequences using divergent primers based on a known region (Triglia T et al (1988) Nucleic Acids Res 16:8186). The primers may be designed using OLIGO® 4.06 Primer Analysis Software (1992; National Biosciences Inc, Plymouth Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Capture PCR (Lagerstrom M et al (1991) PCR Methods Applic 1:111–19) may also be used as a method for PCR amplification of DNA fragments adjacent to a known sequence in human and yeast artificial chromosome DNA. Capture PCR also requires multiple restriction enzyme digestions and ligations to place an engineered double-stranded sequence into an unknown portion of the DNA molecule before PCR.

Another method which may be used to retrieve unknown sequence is walking PCR (Parker J D et al (1991) Nucleic Acids Res 19:3055–60), and which involves targeted gene walking. Alternatively, PCR, nested primers, Promoter-Finder™ (Clontech, Palo Alto Calif.) and PromoterFinder libraries can be used to walk in genomic DNA. This process avoids the need to screen libraries and is useful in finding intron/exon junctions.

Preferred libraries for screening for full length cDNAs are those which have been size-selected to include larger cDNAs. Also, random primed libraries are preferred in that they will contain more sequences which contain the 5' and upstream regions of genes. A randomly primed library may be particularly useful if an oligo d(T) library does not yield a full-length cDNA. Genomic libraries are useful for extension into the 5' nontranslated regulatory region.

Capillary electrophoresis may be used to analyze either the size or confirm the nucleotide sequence in sequencing or PCR products. Systems for rapid sequencing are available from Perkin Elmer, Beckman Instruments (Fullerton Calif.), and other companies. Capillary sequencing may employ flowable polymers for electrophoretic separation, four different fluorescent dyes (one for each nucleotide) which are laser activated, and detection of the emitted wavelengths by a charge coupled device camera. Output/light intensity is converted to electrical signal using appropriate software (eg. Genotyper™ and Sequence Navigator™ from Perkin Elmer) and the entire process from loading of samples to computer analysis and electronic data display is computer controlled. Capillary electrophoresis is particularly suited to the sequencing of small pieces of DNA which might be present in limited amounts in a particular sample. The reproducible sequencing of up to 350 bp of M13 phage DNA in 30 min has been reported (Ruiz-Martinez M C et al (1993) Anal Chem 65:2851–8).

Expression of the Nucleotide Sequence

In accordance with the present invention, polynucleotide sequences which encode HCP, fragments of the polypeptides, fusion proteins or functional equivalents thereof may be used in recombinant DNA molecules that direct the expression of HCP in appropriate host cells. Due to the inherent degeneracy of the genetic code, other DNA sequences which encode substantially the same or a functionally equivalent amino acid sequence, may be used to clone and express HCP. As will be understood by those of skill in the art, it may be advantageous to produce HCP-encoding nucleotide sequences possessing non-naturally occurring codons. Codons preferred by a particular prokaryotic or eukaryotic host (Murray E et al (1989) Nuc Acids Res 17:477–508) can be selected, for example, to increase the rate of HCP expression or to produce recombinant RNA transcripts having desirable properties, such as a longer half-life, than transcripts produced from naturally occurring sequence.

The nucleotide sequences of the present invention can be engineered in order to alter HCP-encoding sequences for a variety of reasons, including but not limited to, alterations which modify the cloning, processing and/or expression of the gene product. For example, mutations may be introduced using techniques which are well known in the art, eg, site-directed mutagenesis to insert new restriction sites, to alter glycosylation patterns, to change codon preference, to produce splice variants, etc.

In another embodiment of the invention, natural, modified or recombinant HCP-encoding sequences may be ligated to heterologous sequences to encode fusion proteins. For example, for screening of peptide libraries for inhibitors of HCP activity, it may be useful to encode a chimeric HCP protein that is recognized by a commercially available antibody. A fusion protein may also be engineered to contain a cleavage site located between an HCP and the heterologous protein sequence, so that the HCP may be cleaved and substantially purified away from the heterologous moiety.

In an alternate embodiment of the invention, the sequences encoding HCP may be synthesized, whole or in part, using chemical methods well known in the art (see Caruthers M H et al (1980) Nuc Acids Res Symp Ser 215–23, Horn T et al (1980) Nuc Acids Res Symp Ser 225–32, etc). Alternatively, the protein itself may be produced using chemical methods to synthesize an HCP amino acid sequence, whole or in part. For example, peptide synthesis can be performed using various solid-phase techniques (Roberge J Y et al (1995) Science 269:202–204) and automated synthesis may be achieved, for example, using the ABI 431A Peptide Synthesizer (Perkin Elmer) in accordance with the instructions provided by the manufacturer.

The newly synthesized peptide can be substantially purified by preparative high performance liquid chromatography (eg, Creighton (1983) *Proteins, Structures and Molecular Principles*, W H Freeman and Co, New York N.Y.). The composition of the synthetic peptides may be confirmed by amino acid analysis or sequencing (eg, the Edman degradation procedure; Creighton, supra). Additionally the amino acid sequences of HCP, or any part thereof, may be altered during direct synthesis and/or combined using chemical methods with sequences from other proteins, or any part thereof, to produce a variant polypeptide.

Expression Systems

In order to express a biologically active HCP, the nucleotide sequence encoding HCP or its functional equivalent, is inserted into an appropriate expression vector, ie, a vector which contains the necessary elements for the transcription and translation of the inserted coding sequence.

Methods which are well known to those skilled in the art can be used to construct expression vectors containing HCP-encoding sequence and appropriate transcriptional or translational controls. These methods include in vitro recombinant DNA techniques, synthetic techniques and in vivo recombination or genetic recombination. Such techniques are described in Sambrook et al (1989) *Molecular Cloning, A Laboratory Manual*, Cold Spring Harbor Press, Plainview N.Y. and Ausubel F M et al (1989) *Current Protocols in Molecular Biology*, John Wiley & Sons, New York N.Y.

A variety of expression vector/host systems may be utilized to contain and express HCP-encoding sequences. These include but are not limited to microorganisms such as bacteria transformed with recombinant bacteriophage, plasmid or cosmid DNA expression vectors; yeast transformed with yeast expression vectors; insect cell systems infected with virus expression vectors (eg, baculovirus); plant cell systems transfected with virus expression vectors (eg, cauliflower mosaic virus, CaMV; tobacco mosaic virus, TMV) or transformed with bacterial expression vectors (eg, Ti or pBR322 plasmid); or animal cell systems.

The "control elements" or "regulatory sequences" of these systems vary in their strength and specificities and are those nontranslated regions of the vector, enhancers, promoters, and 3' untranslated regions, which interact with host cellular proteins to carry out transcription and translation. Depending on the vector system and host utilized, any number of suitable transcription and translation elements, including constitutive and inducible promoters, may be used. For example, when cloning in bacterial systems, inducible promoters such as the hybrid lacZ promoter of the Bluescript® phagemid (Stratagene, La Jolla Calif.) or pSport1 (Gibco BRL) and ptrp-lac hybrids and the like may be used. The baculovirus polyhedrin promoter may be used in insect cells. Promoters or enhancers derived from the genomes of plant cells (eg, heat shock, RUBISCO; and storage protein genes) or from plant viruses (eg, viral promoters or leader sequences) may be cloned into the vector. In mammalian cell systems, promoters from the mammalian genes or from mammalian viruses are most appropriate. If it is necessary to generate a cell line that contains multiple copies of the sequence encoding HCP, vectors based on SV40 or EBV may be used with an appropriate selectable marker.

In bacterial systems, a number of expression vectors may be selected depending upon the use intended for HCP. For example, when large quantities of HCP are needed for the induction of antibodies, vectors which direct high level expression of fusion proteins that are readily purified may be desirable. Such vectors include, but are not limited to, the multifunctional *E. coli* cloning and expression vectors such as Bluescript® (Stratagene), in which the sequence encoding HCP may be ligated into the vector in frame with sequences for the amino-terminal Met and the subsequent 7 residues of β-galactosidase so that a hybrid protein is produced; pIN vectors (Van Heeke & Schuster (1989) J Biol Chem 264:5503–5509); and the like. pGEX vectors (Promega, Madison Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems are designed to include heparin, thrombin or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase and PGH may be used. For reviews, see Ausubel et al (supra) and Grant et al (1987) Methods in Enzymology 153:516–544.

In cases where plant expression vectors are used, the expression of a sequence encoding HCP may be driven by any of a number of promoters. For example, viral promoters such as the 35S and 19S promoters of CaMV (Brisson et al (1984) Nature 310:511–514) may be used alone or in combination with the omega leader sequence from TMV (Takamatsu et al (1987) EMBO J 6:307–311). Alternatively, plant promoters such as the small subunit of RUBISCO (Coruzzi et al (1984) EMBO J 3:1671–1680; Broglie et al (1984) Science 224:838–843); or heat shock promoters (Winter J and Sinibaldi R M (1991) Results Probl Cell Differ 17:85–105) may be used. These constructs can be introduced into plant cells by direct DNA transformation or pathogen-mediated transfection. For reviews of such techniques, see Hobbs S or Murry L E in McGraw Hill *Yearbook of Science and Technology* (1992) McGraw Hill New York N.Y., pp 191–196 or Weissbach and Weissbach (1988) *Methods for Plant Molecular Biology*, Academic Press, New York N.Y., pp 421–463.

An alternative expression system which may be used to express HCP is an insect system. In one such system, *Autographa californica* nuclear polyhedrosis virus (AcNPV) is used as a vector to express foreign genes in *Spodoptera frugiperda* cells or in Trichoplusia larvae. The sequence encoding HCP may be cloned into a nonessential region of the virus, such as the polyhedrin gene, and placed under control of the polyhedrin promoter. Successful insertion of the sequence encoding HCP will render the polyhedrin gene inactive and produce recombinant virus lacking coat protein coat. The recombinant viruses are then used to infect *S. frugiperda* cells or Trichoplusia larvae in which HCP is expressed (Smith et al (1983) J Virol 46:584; Engelhard E K et al (1994) Proc Nat Acad Sci 91:3224–7).

In mammalian host cells, a number of viral-based expression systems may be utilized. In cases where an adenovirus is used as an expression vector, a sequence encoding HCP may be ligated into an adenovirus transcription/translation complex consisting of the late promoter and tripartite leader sequence. Insertion in a nonessential E1 or E3 region of the viral genome will result in a viable virus capable of expressing in infected host cells (Logan and Shenk (1984) Proc Natl Acad Sci 81:3655–59). In addition, transcription enhancers, such as the rous sarcoma virus (RSV) enhancer, may be used to increase expression in mammalian host cells.

Specific initiation signals may also be required for efficient translation of a sequence encoding HCP. These signals include the ATG initiation codon and adjacent sequences. In cases where the sequence encoding HCP, its initiation codon and upstream sequences are inserted into the most appropriate expression vector, no additional translational control signals may be needed. However, in cases where only coding sequence, or a portion thereof, is inserted, exogenous translational control signals including the ATG initiation codon must be provided. Furthermore, the initiation codon must be in the correct reading frame to ensure translation of the entire insert. Exogenous translational elements and initiation codons can be of various origins, both natural and synthetic. The efficiency of expression may be enhanced by the inclusion of enhancers appropriate to the cell system in use (Scharf D et al (1994) Results Probl Cell Differ 20:125–62; Bittner et al (1987) Methods in Enzymol 153:516–544).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation and acylation. Post-translational processing which cleaves a "prepro" form of the protein may also be important for correct insertion, folding and/or function. Different host cells such as CHO, HeLa, MDCK, 293, WI38, etc have specific cellular machinery and characteristic mechanisms for such post-translational activities and may be chosen to ensure the correct modification and processing of the introduced, foreign protein.

For long-term, high-yield production of recombinant proteins, stable expression is preferred. For example, cell lines which stably express HCP may be transformed using expression vectors which contain viral origins of replication or endogenous expression elements and a selectable marker gene. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transformed cells can be proliferated using tissue culture techniques appropriate to the cell type.

Any number of selection systems may be used to recover transformed cell lines. These include, but are not limited to, the herpes simplex virus thymidine kinase (Wigler M et al (1977) Cell 11:223–32) and adenine phosphoribosyltransferase (Lowy I et al (1980) Cell 22:817–23) genes which can be employed in tk- or aprt- cells, respectively. Also, antimetabolite, antibiotic or herbicide resistance can be used as the basis for selection; for example, dhfr which confers resistance to methotrexate (Wigler M et al (1980) Proc Natl Acad Sci 77:3567–70); npt, which confers resistance to the aminoglycosides neomycin and G-418 (Colbere-Garapin F et al (1981) J Mol Biol 150:1–14) and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman S C and R C Mulligan (1988) Proc Natl Acad Sci 85:8047–51). Recently, the use of visible markers has gained popularity with such markers as anthocyanins, β glucuronidase and its substrate, GUS, and luciferase and its substrate, luciferin, being widely used not only to identify transformants, but also to quantify the amount of transient or stable protein expression attributable to a specific vector system (Rhodes C A et al (1995) Methods Mol Biol 55:121–131).

Identification of Transformants Containing the Polynucleotide Sequence

Although the presence/absence of marker gene expression suggests that the gene of interest is also present, its presence and expression should be confirmed. For example, if the sequence encoding HCP is inserted within a marker gene sequence, recombinant cells containing the sequence encoding HCP can be identified by the absence of marker gene function. Alternatively, a marker gene can be placed in tandem with the sequence encoding HCP under the control of a single promoter. Expression of the marker gene in response to induction or selection usually indicates expression of the tandem sequence as well.

Alternatively, host cells which contain the sequence encoding HCP and expressing HCP may be identified by a variety of procedures known to those of skill in the art. These procedures include, but are not limited to, DNA-DNA or DNA-RNA hybridization and protein bioassay or immunoassay techniques which include membrane, solution, or chip based technologies for the detection and/or quantification of the nucleic acid or protein.

The presence of the polynucleotide sequence encoding HCP can be detected by DNA-DNA or DNA-RNA hybridization or amplification using probes, portions or fragments of the sequence encoding HCP. Nucleic acid amplification based assays involve the use of oligonucleotides or oligomers based on the nucleic acid sequence to detect transformants containing DNA or RNA encoding HCP. As used herein "oligonucleotides" or "oligomers" refer to a nucleic acid sequence of at least about 10 nucleotides and as many as about 60 nucleotides, preferably about 15 to 30 nucleotides, and more preferably about 20–25 nucleotides which can be used as a probe or amplimer.

A variety of protocols for detecting and measuring the expression of HCP, using either polyclonal or monoclonal antibodies specific for the protein are known in the art. Examples include enzyme-linked immunosorbent assay (ELISA), radioimmunoassay (RIA) and fluorescent activated cell sorting (FACS). A two-site, monoclonal-based immunoassay utilizing monoclonal antibodies reactive to two non-interfering epitopes on HCP is preferred, but a competitive binding assay may be employed. These and other assays are described, among other places, in Hampton R et al (1990, Serological Methods, a Laboratory Manual, APS Press, St Paul Minn.) and Maddox D E et al (1983, J Exp Med 158:1211).

A wide variety of labels and conjugation techniques are known by those skilled in the art and can be used in various nucleic acid and amino acid assays. Means for producing labeled hybridization or PCR probes for detecting related sequences include oligolabeling, nick translation, end-labeling or PCR amplification using a labeled nucleotide. Alternatively, the HCP-encoding sequence, or any portion of it, may be cloned into a vector for the production of an mRNA probe. Such vectors are known in the art, are commercially available, and may be used to synthesize RNA probes in vitro by addition of an appropriate RNA polymerase such as T7, T3 or SP6 and labeled nucleotides.

A number of companies such as Pharmacia Biotech (Piscataway N.J.), Promega (Madison Wis.), and U.S. Biochemical Corp (Cleveland Ohio) supply commercial kits and protocols for these procedures. Suitable reporter molecules or labels include those radionuclides, enzymes, fluorescent, chemiluminescent, or chromogenic agents as well as substrates, cofactors, inhibitors, magnetic particles and the like. Patents teaching the use of such labels include U.S. Pat. Nos. 3,817,837; 3,850,752; 3,939,350; 3,996,345; 4,277,437; 4,275,149 and 4,366,241. Also, recombinant immunoglobulins may be produced as shown in U.S. Pat. No. 4,816,567 incorporated herein by reference.

Purification of HCP

Host cells transformed with a nucleotide sequence encoding HCP may be cultured under conditions suitable for the expression and recovery of the encoded protein from cell culture. The protein produced by a recombinant cell may be secreted or contained intracellularly depending on the sequence and/or the vector used. As will be understood by those of skill in the art, expression vectors containing an HCP-encoding sequence can be designed with signal sequences which direct secretion of HCP through a prokaryotic or eukaryotic cell membrane. Other recombinant constructions may join the sequence encoding HCP to nucleotide sequence encoding a polypeptide domain which will facilitate purification of soluble proteins (Kroll D J et al (1993) DNA Cell Biol 12:441–53; cf discussion of vectors infra containing fusion proteins).

HCP may also be expressed as a recombinant protein with one or more additional polypeptide domains added to facilitate protein purification. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp, Seattle Wash.). The inclusion of a cleavable linker sequence such as Factor XA or enterokinase (Invitrogen, San Diego Calif.) between the purification domain and HCP is useful to facilitate purification. One such expression vector provides for expression of a fusion protein comprising the sequence encoding HCP and nucleic acid sequence encoding 6 histidine residues followed by thioredoxin and an enterokinase cleavage site. The histidine residues facilitate purification while the enterokinase cleavage site provides a means for purifying HCP from the fusion protein.

In addition to recombinant production, fragments of HCP may be produced by direct peptide synthesis using solid-phase techniques (cf Stewart et al. (1969) Solid-Phase Peptide Synthesis, W H Freeman Co, San Francisco; Merrifield J (1963) J Am Chem Soc 85:2149–2154). In vitro protein synthesis may be performed using manual techniques or by automation. Automated synthesis may be achieved, for example, using Applied Biosystems 431A Peptide Synthesizer (Perkin Elmer, Foster City Calif.) in accordance with the instructions provided by the manufacturer. Various fragments of HCP may be chemically synthesized separately and combined using chemical methods to produce the full length molecule.

Uses of HCP

HCPs play a role in processes that involve proteolysis of specific proteins and tissues in local microenvironments including inflammation, metastasis and peptide and proenzyme processing. Since the increased expression and differential regulation of these proteases is linked to the metastatic potential of a variety of cancers, HCPs can be used to intervene in the metastatic process. Similarly, the level and effect of the cathepsins associated with protein processing diseases such as Alzheimer's disease, Huntington's disease, mucolipidosis and arthritic inflammation may be modulated to ameliorate the progression of these diseases.

A therapeutic composition comprising antagonists, inhibitors, antisense molecules or anti-HCP antibodies may have application in the prevention and treatment of individuals susceptible to diseases characterized by excessive HCPs activity. Examples include, but are not limited to, tumors, arthritic inflammations, abnormal protein processing in brain diseases and abnormal processing of regulatory proteins. A therapeutic composition comprised of agonists which modulate the activity of HCPs may have applications in diseases characterized by cathepsin deficiencies including, but not limited to, mucolipidosis I and II.

In another embodiment of the present invention, HCPs may be used to localize and quantitate the expression of HCPs with HCP-specific antibodies and nucleic acid probes based on their sequence. This use has specific prognostic value in a variety of diseases. The correlation between high concentrations of HCPs in primary tumor cells and further occurrence of metastasis would allow the identification of specific node negative breast cancer patients where chemotherapy is indicated. This prognostic potential of HCPs can also be applied to cancers of other organs including, but not limited to, the prostate and bladder.

HCP Antibodies

HCP-specific antibodies are useful for the diagnosis and treatment of conditions and diseases associated with expression of HCP. Such antibodies include, but are not limited to, polyclonal, monoclonal, chimeric, single chain, Fab fragments and fragments produced by a Fab expression library. Neutralizing antibodies, ie, those which inhibit dimer formation, are especially preferred for diagnostics and therapeutics.

The portion of HCP used for antibody induction does not need to have biological activity; however, it must be antigenic. Peptides used to induce specific antibodies may have an amino acid sequence consisting of at least five amino acids, and preferably at least 10 amino acids. Preferably, they should mimic a portion of the amino acid sequence of the natural protein and may contain the entire amino acid sequence of a small, naturally occurring molecule. Short stretches of HCP amino acids may be fused with those of another protein such as keyhole limpet hemocyanin and antibody produced against the chimeric molecule. Procedures well known in the art can be used for the production of antibodies to HCP.

For the production of antibodies, various hosts including goats, rabbits, rats, mice, etc may be immunized by injection with HCP or any portion, fragment or oligopeptide which retains immunogenic properties. Depending on the host species, various adjuvants may be used to increase immunological response. Such adjuvants include but are not limited to Freund's, mineral gels such as aluminum hydroxide, and surface active substances such as lysolecithin, pluronic polyols, polyanions, peptides, oil emulsions, keyhole limpet hemocyanin, and dinitrophenol. BCG (bacilli Calmette-Guerin) and *Corynebacterium parvum* are potentially useful human adjuvants.

Monoclonal antibodies to HCP may be prepared using any technique which provides for the production of antibody molecules by continuous cell lines in culture. These include but are not limited to the hybridoma technique originally described by Koehler and Milstein (1975 Nature 256:495–497), the human B-cell hybridoma technique (Kosbor et al (1983) Immunol Today 4:72; Cote et al (1983) Proc Natl Acad Sci 80:2026–2030) and the EBV-hybridoma technique (Cole et al (1985) *Monoclonal Antibodies and Cancer Therapy*, Alan R Liss Inc, New York N.Y., pp 77–96).

In addition, techniques developed for the production of "chimeric antibodies", the splicing of mouse antibody genes to human antibody genes to obtain a molecule with appropriate antigen specificity and biological activity can be used (Morrison et al (1984) Proc Natl Acad Sci 81:6851–6855; Neuberger et al (1984) Nature 312:604–608; Takeda et al (1985) Nature 314:452–454). Alternatively, techniques described for the production of single chain antibodies (U.S. Pat. No. 4,946,778) can be adapted to produce HCP-specific single chain antibodies.

Antibodies may also be produced by inducing in vivo production in the lymphocyte population or by screening recombinant immunoglobulin libraries or panels of highly specific binding reagents as disclosed in Orlandi et al (1989, Proc Natl Acad Sci 86: 3833–3837), and Winter G and Milstein C (1991; Nature 349:293–299).

Antibody fragments which contain specific binding sites for HCP may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse W D et al (1989) Science 256:1275–1281).

A variety of protocols for competitive binding or immunoradiometric assays using either polyclonal or monoclonal antibodies with established specificities are well known in the art. Such immunoassays typically involve the formation of complexes between HCP and its specific antibody and the measurement of complex formation. A two-site, monoclonal-based immunoassay utilizing monoclonal antibodies reactive to two noninterfering epitopes on a specific HCP protein is preferred, but a competitive binding assay may also be employed. These assays are described in Maddox D E et al (1983, J Exp Med 158:1211).

Diagnostic Assays Using HCP Specific Antibodies

Particular HCP antibodies are useful for the diagnosis of conditions or diseases characterized by expression of HCP or in assays to monitor patients being treated with HCP, its fragments, agonists, antagonists or inhibitors. Diagnostic assays for HCP include methods utilizing the antibody and a label to detect HCP in human body fluids or extracts of cells or tissues. The polypeptides and antibodies of the present invention may be used with or without modification. Frequently, the polypeptides and antibodies will be labeled by joining them, either covalently or noncovalently, with a reporter molecule. A wide variety of reporter molecules are known, several of which were described above.

A variety of protocols for measuring HCP, using either polyclonal or monoclonal antibodies specific for the respective proteins are known in the art. Examples include enzyme-linked immunosorbent assay (ELISA), radioimmunoassay (RIA) and fluorescent activated cell sorting (FACS). A two-site, monoclonal-based immunoassay utilizing monoclonal antibodies reactive to two non-interfering epitopes on HCP is preferred, but a competitive binding assay may be employed. These assays are described, among other places, in Maddox, D E et al (1983, J Exp Med 158:1211).

In order to provide a basis for diagnosis, normal or standard values for HCP expression must be established. This is accomplished by combining body fluids or cell extracts taken from normal subjects, either animal or human, with antibody to HCP under conditions suitable for complex formation which are well known in the art. The amount of standard complex formation may be quantified by comparing various artificial membranes containing known quantities of HCP with both control and disease samples from biopsied tissues. Then, standard values obtained from normal samples may be compared with values obtained from samples from subjects potentially affected by disease. Deviation between standard and subject values establishes the presence of disease state.

Drug Screening

HCP, its catalytic or immunogenic fragments or oligopeptides thereof, can be used for screening therapeutic compounds in any of a variety of drug screening techniques. The fragment employed in such a test may be free in solution, affixed to a solid support, borne on a cell surface, or located intracellularly. The formation of binding complexes, between HCP and the agent being tested, may be measured.

Another technique for drug screening which may be used for high throughput screening of compounds having suitable binding affinity to the HCP is described in detail in "Determination of Amino Acid Sequence Antigenicity" by Geysen H N, WO Application 84/03564, published on Sep. 13, 1984, and incorporated herein by reference. In summary, large numbers of different small peptide test compounds are synthesized on a solid substrate, such as plastic pins or some other surface. The peptide test compounds are reacted with fragments of HCP and washed. Bound HCP is then detected by methods well known in the art. Substantially purified HCP can also be coated directly onto plates for use in the aforementioned drug screening techniques. Alternatively, non-neutralizing antibodies can be used to capture the peptide and immobilize it on a solid support.

This invention also contemplates the use of competitive drug screening assays in which neutralizing antibodies capable of binding HCP specifically compete with a test compound for binding HCP. In this manner, the antibodies can be used to detect the presence of any peptide which shares one or more antigenic determinants with HCP.

Uses of tie Polynucleotide Encoding HCP

A polynucleotide sequence encoding HCP or any part thereof may be used for diagnostic and/or therapeutic purposes. For diagnostic purposes, the sequence encoding HCP of this invention may be used to detect and quantitate gene expression in biopsied tissues in which HCP may be expressed. The diagnostic assay is useful to distinguish between absence, presence, and excess expression of HCP and to monitor regulation of HCP levels during therapeutic intervention. Included in the scope of the invention are oligonucleotide sequences, antisense RNA and DNA molecules, and PNAs.

Another aspect of the subject invention is to provide for hybridization or PCR probes which are capable of detecting polynucleotide sequences, including genomic sequences, encoding HCP or closely related molecules. The specificity of the probe, whether it is made from a highly specific region, eg, 10 unique nucleotides in the 5' regulatory region, or a less specific region, eg, especially in the 3' region, and the stringency of the hybridization or amplification (maximal, high, intermediate or low) will determine whether the probe identifies only naturally occurring HCP, alleles or related sequences.

Probes may also be used for the detection of related sequences and should preferably contain at least 50% of the nucleotides from any of these HCP-encoding sequences. The hybridization probes of the subject invention may be derived from the nucleotide sequence of SEQ ID NO:2 and SEQ ID NO:4 or from genomic sequence including promoter, enhancer elements and introns of the naturally occurring sequences encoding HCP. Hybridization probes may be labeled by a variety of reporter groups, including radionuclides such as 32P or 35S, or enzymatic labels such as alkaline phosphatase coupled to the probe via avidin/biotin coupling systems, and the like.

Other means for producing specific hybridization probes for DNAs include the cloning of nucleic acid sequences encoding HCP or HCP derivatives into vectors for the production of mRNA probes. Such vectors are known in the art and are commercially available and may be used to synthesize RNA probes in vitro by means of the addition of the appropriate RNA polymerase as T7 or SP6 RNA polymerase and the appropriate radioactively labeled nucleotides.

Diagnostic Use

Polynucleotide sequences encoding HCP may be used for the diagnosis of conditions or diseases with which the expression of HCP is associated. For example, polynucleotide sequences encoding HCP may be used in hybridization or PCR assays of fluids or tissues from biopsies to detect HCP expression. The form of such qualitative or quantitative methods may include Southern or northern analysis, dot blot or other membrane-based technologies; PCR technologies; dip stick, pin, chip and ELISA technologies. All of these techniques are well known in the art and are the basis of many commercially available diagnostic kits.

The HCP-encoding nucleotide sequences disclosed herein provide the basis for assays that detect activation or induction associated with inflammation or disease. The nucleotide sequence may be labeled by methods known in the art and added to a fluid or tissue sample from a patient under conditions suitable for the formation of hybridization complexes. After an incubation period, the sample is washed with a compatible fluid which optionally contains a dye (or other label requiring a developer) if the nucleotide has been labeled with an enzyme. After the compatible fluid is rinsed off, the dye is quantitated and compared with a standard. If the amount of dye in the biopsied or extracted sample is significantly elevated over that of a comparable control sample, the nucleotide sequence has hybridized with nucleotide sequences in the sample, and the presence of elevated levels of nucleotide sequences encoding HCP in the sample indicates the presence of the associated inflammation and/or disease.

Such assays may also be used to evaluate the efficacy of a particular therapeutic treatment regime in animal studies, in clinical trials, or in monitoring the treatment of an individual patient. In order to provide a basis for the diagnosis of disease, a normal or standard profile for HCP expression must be established. This is accomplished by combining body fluids or cell extracts taken from normal subjects, either animal or human, with HCP, or a portion thereof, under conditions suitable for hybridization or amplification. Standard hybridization may be quantified by comparing the values obtained for normal subjects with a dilution series of HCP run in the same experiment where a known amount of substantially purified HCP is used. Standard values obtained from normal samples may be compared with values obtained from samples from patients affected by HCP-associated diseases. Deviation between standard and subject values establishes the presence of disease.

Once disease is established, a therapeutic agent is administered and a treatment profile is generated. Such assays may be repeated on a regular basis to evaluate whether the values in the profile progress toward or return to the normal or standard pattern. Successive treatment profiles may be used to show the efficacy of treatment over a period of several days or several months.

PCR may be used as described in U.S. Pat. Nos. 4,683,195 and 4,965,188 and provides additional uses for oligonucleotides based upon the sequences encoding HCP. Such oligomers are generally chemically synthesized, but they may be generated enzymatically or produced from a recombinant source. Oligomers generally comprise two nucleotide sequences, one with sense orientation (5'→3') and one with antisense (3'←5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Additionally, methods which may be used to quantitate the expression of a particular molecule include radiolabeling (Melby P C et al 1993 J Immunol Methods 159:235–44) or biotinylating (Duplaa C et al 1993 Anal Biochem 229–36) nucleotides, coamplification of a control nucleic acid, and standard curves onto which the experimental results are interpolated. Quantitation of multiple samples may be speeded up by running the assay in an ELISA format where the oligomer of interest is presented in various dilutions and a spectrophotometric or colorimetric response gives rapid quantitation. A definitive diagnosis of this type may allow health professionals to begin aggressive treatment and prevent further worsening of the condition. Similarly, further assays can be used to monitor the progress of a patient during treatment. Furthermore, the nucleotide sequences disclosed herein may be used in molecular biology techniques that have not yet been developed, provided the new techniques rely on properties of nucleotide sequences that are currently known such as the triplet genetic code, specific base pair interactions, and the like.

Therapeutic Use

Based upon the homology between HCP-1 and GI 555662 and HCP-2 and GI 181180 and their expression profiles, the polynucleotide encoding HCPs disclosed herein may be useful in the treatment of diseases including cancers and inflammation and in diseases with components involving protein processing.

Expression vectors derived from retroviruses, adenovirus, herpes or vaccinia viruses, or from various bacterial plasmids, may be used for delivery of nucleotide sequences to the targeted organ, tissue or cell population. Methods which are well known to those skilled in the art can be used to construct recombinant vectors which will express antisense of the sequence encoding HCP. See, for example, the techniques described in Sambrook et al (supra) and Ausubel et al (supra).

The polynucleotides comprising full length cDNA sequence and/or its regulatory elements enable researchers to use the sequence encoding HCP as an investigative tool in sense (Youssoufian H and HF Lodish 1993 Mol Cell Biol 13:98–104) or antisense (Eguchi et al (1991) Annu Rev Biochem 60:631–652) regulation of gene function. Such technology is now well known in the art, and sense or antisense oligomers, or larger fragments, can be designed from various locations along the coding or control regions.

Genes encoding HCP can be turned off by transfecting a cell or tissue with expression vectors which express high levels of a desired HCP fragment. Such constructs can flood cells with untranslatable sense or antisense sequences. Even in the absence of integration into the DNA, such vectors may continue to transcribe RNA molecules until all copies are disabled by endogenous nucleases. Transient expression may last for a month or more with a non-replicating vector (Mettler I, personal communication) and even longer if appropriate replication elements are part of the vector system.

As mentioned above, modifications of gene expression can be obtained by designing antisense molecules, DNA, RNA or PNA, to the control regions of the sequence encoding HCP, ie, the promoters, enhancers, and introns. Oligonucleotides derived from the transcription initiation site, eg, between −10 and +10 regions of the leader sequence, are preferred. The antisense molecules may also be designed to block translation of mRNA by preventing the transcript from binding to ribosomes. Similarly, inhibition can be achieved using "triple helix" base-pairing methodology. Triple helix pairing compromises the ability of the double helix to open sufficiently for the binding of polymerases, transcription factors, or regulatory molecules. Recent therapeutic advances using triplex DNA were reviewed by Gee J E et al (In: Huber B E and B I Carr (1994) *Molecular and Immunologic Approaches*, Futura Publishing Co, Mt Kisco N.Y.).

Ribozymes are enzymatic RNA molecules capable of catalyzing the specific cleavage of RNA. The mechanism of ribozyme action involves sequence-specific hybridization of the ribozyme molecule to complementary target RNA, followed by endonucleolytic cleavage. Within the scope of the invention are engineered hammerhead motif ribozyme molecules that can specifically and efficiently catalyze endonucleolytic cleavage of the sequence encoding HCP.

Specific ribozyme cleavage sites within any potential RNA target are initially identified by scanning the target molecule for ribozyme cleavage sites which include the following sequences, GUA, GUU and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Antisense molecules and ribozymes of the invention may be prepared by any method known in the art for the synthesis of RNA molecules. These include techniques for chemically synthesizing oligonucleotides such as solid phase phosphoramidite chemical synthesis. Alternatively, RNA molecules may be generated by in vitro and in vivo transcription of DNA sequences encoding HCP. Such DNA sequences may be incorporated into a wide variety of vectors with suitable RNA polymerase promoters such as T7 or SP6. Alternatively, antisense cDNA constructs that synthesize antisense RNA constitutively or inducibly can be introduced into cell lines, cells or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine and wybutosine as well as acetyl-, methyl-, thio- and similarly modified forms of adenine, cytidine, guanine, thymine, and uridine which are not as easily recognized by endogenous endonucleases.

Methods for introducing vectors into cells or tissues include those methods discussed infra and which are equally suitable for in vivo, in vitro and ex viva therapy. For ex vivo therapy, vectors are introduced into stem cells taken from the patient and clonally propagated for autologous transplant back into that same patient as presented in U.S. Pat. Nos. 5,399,493 and 5,437,994, disclosed herein by reference. Delivery by transfection and by liposome are quite well known in the art.

Furthermore, the nucleotide sequences encoding HCP disclosed herein may be used in molecular biology techniques that have not yet been developed, provided the new techniques rely on properties of nucleotide sequences that are currently known, including but not limited to such properties as the triplet genetic code and specific base pair interactions.

Detection and Mapping of Related Polynucleotide Sequences

The nucleic acid sequences encoding HCP can also be used to generate hybridization probes for mapping the naturally occurring genomic sequence. The sequence may be mapped to a particular chromosome or to a specific region of the chromosome using well known techniques. These include in situ hybridization to chromosomal spreads, flow-sorted chromosomal preparations, or artificial chromosome constructions such as yeast artificial chromosomes, bacterial artificial chromosomes, bacterial P1 constructions or single chromosome cDNA libraries as reviewed in Price C M (1993; Blood Rev 7:127–34) and Trask B J (1991; Trends Genet 7:149–54).

The technique of fluorescent in situ hybridization of chromosome spreads has been described, among other places, in Verma et al (1988) *Human Chromosomes: A Manual of Basic Techniques*, Pergamon Press, New York N.Y. Fluorescent in situ hybridization of chromosomal preparations and other physical chromosome mapping techniques may be correlated with additional genetic map data.

Examples of genetic map data can be found in the 1994 Genome Issue of Science (265:1981f). Correlation between the location of a the sequence encoding HCP on a physical chromosomal map and a specific disease (or predisposition to a specific disease) may help delimit the region of DNA associated with that genetic disease. The nucleotide sequences of the subject invention may be used to detect differences in gene sequences between normal, carrier or affected individuals.

In situ hybridization of chromosomal preparations and physical mapping techniques such as linkage analysis using established chromosomal markers are invaluable in extending genetic maps. A recent example of an STS based map of the human genome was recently published by the Whitehead-MIT Center for Genomic Research (Hudson T J et al (1995) Science 270:1945–1954). Often the placement of a gene on the chromosome of another mammalian species such as mouse (Whitehead Institute/MIT Center for Genome Research, Genetic Map of the Mouse, Database Release 10, Apr. 28, 1995) may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once a disease or syndrome, such as ataxia telangiectasia (AT), has been crudely localized by genetic linkage to a particular genomic region, for example, AT to 11q22–23 (Gatti et al (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier or affected individuals.

Pharmaceutical Compositions

The present invention relates to pharmaceutical compositions which may comprise nucleotides, proteins, antibodies, agonists, antagonists, or inhibitors, alone or in combination with at least one other agent, such as stabilizing compound, which may be administered in any sterile, biocompatible pharmaceutical carrier, including, but not limited to, saline, buffered saline, dextrose, and water. Any of these molecules can be administered to a patient alone, or in combination with other agents, drugs or hormones, in pharmaceutical compositions where it is mixed with excipient(s) or pharmaceutically acceptable carriers. In one embodiment of the present invention, the pharmaceutically acceptable carrier is pharmaceutically inert.

Administration of Pharmaceutical Compositions

Administration of pharmaceutical compositions is accomplished orally or parenterally. Methods of parenteral delivery include topical, intra-arterial (directly to the tumor), intramuscular, subcutaneous, intramedullary, intrathecal, intraventricular, intravenous, intraperitoneal, or intranasal administration. In addition to the active ingredients, these pharmaceutical compositions may contain suitable pharmaceutically acceptable carriers comprising excipients and auxiliaries which facilitate processing of the active compounds into preparations which can be used pharmaceutically. Further details on techniques for formulation and administration may be found in the latest edition of "Remington's Pharmaceutical Sciences" (Maack Publishing Co, Easton Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, or other plants; cellulose such as methyl cellulose, hydroxypropylmethylcellulose, or sodium carboxymethylcellulose; and gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, ie, dosage.

Pharmaceutical preparations which can be used orally include push-fit capsules made of gelatin, as well as soft, sealed capsules made of gelatin and a coating such as glycerol or sorbitol. Push-fit capsules can contain active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Pharmaceutical formulations for parenteral administration include aqueous solutions of active compounds. For injection, the pharmaceutical compositions of the invention may be formulated in aqueous solutions, preferably in physiologically compatible buffers such as Hanks's solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

Manufacture and Storage

The pharmaceutical compositions of the present invention may be manufactured in a manner that is known in the art, eg, by means of conventional mixing, dissolving, granulating, dragee-making, levigating, emulsifying, encapsulating, entrapping or lyophilizing processes.

The pharmaceutical composition may be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM–50 mM histidine, 0.1%–2% sucrose, 2%–7% mannitol at a pH range of 4.5 to 5.5 that is combined with buffer prior to use.

After pharmaceutical compositions comprising a compound of the invention formulated in an acceptable carrier have been prepared, they can be placed in an appropriate container and labeled for treatment of an indicated condition. For administration of HCP, such labeling would include amount, frequency and method of administration.

Therapeutically Effective Dose

Pharmaceutical compositions suitable for use in the present invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, eg, of neoplastic cells, or in animal models, usually mice, rabbits, dogs, or pigs. The animal model is also used to achieve a desirable concentration range and route of administration. Such Information can then be used to determine useful doses and routes for administration in humans.

A therapeutically effective dose refers to that amount of protein or its antibodies, antagonists, or inhibitors which ameliorate the symptoms or condition. Therapeutic efficacy and toxicity of such compounds can be determined by standard pharmaceutical procedures in cell cultures or experimental animals, eg, ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50. Pharmaceutical compositions which exhibit large therapeutic indices are preferred. The data obtained from cell culture assays and animal studies is used in formulating a range of dosage for human use. The dosage of such compounds lies preferably within a range of circulating concentrations that include the ED50 with little or no toxicity. The dosage varies within this range depending upon the dosage form employed, sensitivity of the patient, and the route of administration.

The exact dosage is chosen by the individual physician in view of the patient to be treated. Dosage and administration are adjusted to provide sufficient levels of the active moiety or to maintain the desired effect. Additional factors which may be taken into account include the severity of the disease state, eg, tumor size and location; age, weight and gender of the patient; diet, time and frequency of administration, drug combination(s), reaction sensitivities, and tolerance/response to therapy. Long acting pharmaceutical compositions might be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature. See U.S. Pat. Nos. 4,657,760; 5,206,344; or 5,225,212. Those skilled in the art will employ different formulations for nucleotides than for proteins or their inhibitors. Similarly, delivery of polynucleotides or polypeptides will be specific to particular cells, conditions, locations, etc.

The examples below are provided to illustrate the subject invention and are not included for the purpose of limiting the invention.

EXAMPLES

I cDNA Library Construction

HCP-1

The cDNA library FIBRAGT02 was constructed from fibroblast cell lines derived from skin explants taken from the triceps area of an ataxia telangiectasia (AT) patient. The explants were cultured, tested for contamination and stored as described in Weeks et al. (1991) Rad Res 128:90–99.

Samples from each line were cultured for 14 passages and treated in late log growth phase (5 days post 1:3 split) as a monolayer in 150 mm petri plates. Because AT cells are highly sensitive to radiation, equivalent dosages were determined experimentally for each cell line: D10=126+5cGy for AT fibroblasts; D10=563+31cGy for normal fibroblasts.

For normal fibroblasts, about $8.25 \times 10^7$ cells were sham-irradiated and then incubated for 5 min (22 plates) or 30 min (23 plates) at 37° C. These two sets of untreated or control cells were combined and harvested. Five minute post-gamma irradiation treatments consisted of exposing 43 plates containing about $8.49 \times 10^7$ normal cells to 50cGy from a Cs137 source and incubating them at 37° C. for five minutes before harvesting. Thirty minute post-gamma irradiation treatments consisted of exposing 43 plates containing about $8.36 \times 10^7$ normal cells to 50cGy from the Cs137 source and incubating them at 37+ C. for thirty minutes before harvesting.

For AT fibroblasts, about $9.45 \times 10^7$ cells, were sham-irradiated and then incubated for 5 min (22 plates) or 30 min (23 plates) at 37° C. These two sets of plates (hereafter known as untreated or control AT cells) were combined and harvested. Five minute post-gamma irradiation treatments consisted of exposing 43 plates containing about $1.07 \times 10^8$ AT cells to 50cGy from a Cs137 source and incubating them at 37° C. for five minutes before harvesting. Thirty minute post-gamma irradiation treatments consisted of exposing 43 plates containing about $9.71 \times 10^7$ AT cells to 50cGy from the Cs137 source and incubating them at 37° C. for thirty minutes before harvesting.

The RNA was prepared by the hot phenol method and enriched for polyadenylated (poly-A) RNA by oligo d(T)-cellulose chromatography (Godbout et al. (1988) Mol Cell Biol 8:1169–1178). The yields varied from 3.0 to 5.0 percent of the total RNA. The poly-A RNA was visualized on an agarose gel, quantified, and sent to Stratagene (La Jolla Calif.) where the cDNA libraries were constructed in the Uni-ZAP™ vector system.

HCP-2

The cDNA library LUNGNOT02 was constructed from the normal lung tissue of a 47 year old male Caucasian (HEV062). The tissue was obtained from Keystone Skin Bank, International Institute for the Advancement of Medicine (Exton, Pa.). The frozen tissue was ground in a mortar and pestle and lysed immediately in a buffer containing guanidinium isothiocyanate. The lysate was extracted twice with phenol chloroform at pH 8.0 and centrifuged over a CsCl cushion using an Beckman SW28 rotor in a Beckman L8-70M Ultracentrifuge (Beckman Instruments). The RNA was precipitated using 0.3 M sodium acetate and 2.5 volumes of ethanol, resuspended in water and DNase treated for 15 min at 37° C. The poly A+ RNA was isolated using the Qiagen Oligotex kit (QIAGEN Inc, Chatsworth Calif.).

For both FIBRAGT02 and LUNGNOT02, first strand cDNA synthesis was accomplished using an oligo d(T) primer/linker which also contained an XhoI restriction site. Second strand synthesis was performed using a combination of DNA polymerase I, E. coli ligase and RNase H, followed by the addition of an EcoRI adaptor to the blunt ended cDNA. The EcoRI adapted, double-stranded cDNA was then digested with XhoI restriction enzyme and fractionated on Sephacryl S400 to obtain sequences which exceeded 1000 bp in size. The size selected cDNAs were inserted into the UniZap® vector system (Stratagene, La Jolla Calif.); and the vector, which contains the pBluescript™ phagemid (Stratagene), was transformed into cells of E. coli, strain XL1-BlueMRF™ (Stratagene).

The phagemid forms of individual cDNA clones were obtained by the invivo excision process. Enzymes from both pBluescript and a cotransformed f1 helper phage nicked the DNA, initiated new DNA synthesis, and created the smaller, single-stranded circular phagemid DNA molecules which contained the cDNA insert. The phagemid DNA was released, purified, and used to reinfect fresh host cells (SOLR, Stratagene). Presence of the phagemid which carries the gene for β-lactamase allowed transformed bacteria to grow on medium containing ampicillin.

II Isolation and Sequencing of cDNA Clones

HCP-1

Phagemid DNA for the FIBRAGT02 library was purified using the MAGIC MINIPREPS™ DNA purification system (catalogue #A7100, Promega Corp., Madison Wis.). This small-scale process provides a simple and reliable method for lysing the bacterial cells and rapidly isolating purified phagemid DNA using a proprietary DNA-binding resin. The DNA was eluted from the purification resin already prepared for DNA sequencing and other analytical manipulations.

Alternatively, phagemid DNA may be purified using the QIAWELL-8 Plasmid, QIAWELL PLUS and QIAWELL ULTRA DNA purification systems (QIAGEN, Chatsworth, Calif.). The DNA was eluted from the purification resin and prepared for DNA sequencing and other analytical manipulations.

Plasmid DNA for the LUNGNOT02 library was purified using the Miniprep Kit (Catalogue # 77468, Advanced Genetic Technologies Corporation, Gaithersburg Md.), a 96-well block kit with reagents for 960 purifications. The recommended protocol included with the kit was employed except for the following changes. Each of the 96 wells was filled with only 1 ml of sterile Terrific Broth (Catalog # 22711, LIFE TECHNOLOGIES™) with carbenicill n at 25 mg/L and glycerol at 0.4%. After the wells were inoculated, the bacteria were cultured for 24 hours and lysed with 60 μl of lysis buffer. A centrifugation step (Beckman GS-6R @2900 rpm for 5 min; Beckman Instruments) was performed before the contents of the block were added to the primary filter plate. The optional step of adding isopropanol to TRIS buffer was not routinely performed. After the last step in the protocol, samples were transferred to a Beckman 96-well block for storage.

The cDNAs were sequenced by the method of Sanger F and A R Coulson (1975; J Mol Biol 94:441f), using a Hamilton Micro Lab 2200 (Hamilton, Reno Nev.) in combination with four Peltier Thermal Cyclers (PTC200 from MJ Research, Watertown Mass.) and Applied Biosystems 377 or 373 DNA Sequencing Systems (Perkin Elmer) and reading frame was determined.

III Homology Searching of cDNA Clones and Their Deduced Proteins

Each cDNA was compared to sequences in GenBank using a search algorithm developed by Applied Biosystems and incorporated into the INHERIT™ 670 Sequence Analysis System. In this algorithm, Pattern Specification Language (TRW Inc, Los Angeles Calif.) was used to determine regions of homology. The three parameters that determine how the sequence comparisons run were window size, window offset, and error tolerance. Using a combination of these three parameters, the DNA database was searched for sequences containing regions of homology to the query sequence, and the appropriate sequences were scored with an initial value. Subsequently, these homologous regions were examined using dot matrix homology plots to distinguish regions of homology from chance matches. Smith-Waterman alignments were used to display the results of the homology search.

Peptide and protein sequence homologies were ascertained using the INHERIT™ 670 Sequence Analysis System in a way similar to that used in DNA sequence homologies. Pattern Specification Language and parameter windows were used to search protein databases for sequences containing regions of homology which were scored with an initial value. Dot-matrix homology plots were examined to distinguish regions of significant homology from chance matches.

BLAST, which stands for Basic Local Alignment Search Tool (Altschul S F (1993) J Mol Evol 36:290–300; Altschul, S F et al (1990) J Mol Biol 215:403–10), was used to search for local sequence alignments. BLAST produces alignments of both nucleotide and amino acid sequences to determine sequence similarity. Because of the local nature of the alignments, BLAST is especially useful in determining exact matches or in identifying homologs. BLAST is useful for matches which do not contain gaps. The fundamental unit of BLAST algorithm output is the High-scoring Segment Pair (HSP).

An HSP consists of two sequence fragments of arbitrary but equal lengths whose alignment is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

IV Northern Analysis

Northern analysis is a laboratory technique used to detect the presence of a transcript of a gene and involves the hybridization of a labeled nucleotide sequence to a membrane on which RNAs from a particular cell type or tissue have been bound (Sambrook et al. supra).

Analogous computer techniques using BLAST (Altschul SF 1993 and 1990, supra) are used to search for identical or related molecules in nucleotide databases such as GenBank or the LIFESEQ™ database (Incyte, Palo Alto Calif.). This analysis is much faster than multiple, membrane-based hybridizations. In addition, the sensitivity of the computer search can be modified to determine whether any particular match is categorized as exact or homologous.

The basis of the search is the product score which is defined as:

$$\frac{\% \text{ sequence identity} \times \% \text{ maxium BLAST score}}{100}$$

and it takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

The results of the search are reported as a list of libraries in which the full length sequence, or parts thereof, is represented, the abundance of the sequence, and the percent abundance. Abundance directly reflects the number of times a particular transcript is present in a cDNA library, and percent abundance is abundance divided by the number of sequences examined in the library. ps V Extension of the Sequences Encoding HCP The nucleic acid sequence of SEQ ID NO:2 and SEQ ID NO:4 is used to design oligo-nucleotide primers for extending a partial nucleotide sequence to full length or for obtaining 5'sequence from genomic libraries. One primer is synthesized to initiate extension in the antisense direction (XLR) and the other is synthesized to extend sequence in the sense direction (XLF). Primers allow the extension of the known sequence "outward" generating amplicons containing new, unknown nucleotide sequence for the region of interest. The initial primers are designed from the cDNA using OLIGO® 4.06 Primer Analysis Software (National Biosciences), or another appropriate program, to be 22–30 nucleotides in length, to have a GC content of 50% or more, and to anneal to the target sequence at temperatures about $68°–72°$ C. Any stretch of nucleotides which would result in hairpin structures and primer-primer dimerizations is avoided.

The original, selected cDNA libraries, or a human genomic library are used to extend the sequence; the latter is most useful to obtain 5' upstream regions. If more extension is necessary or desired, additional sets of primers are designed to further extend the known region.

By following the instructions for the XL-PCR kit (Perkin Elmer) and thoroughly mixing the enzyme and reaction mix, high fidelity amplification is obtained. Beginning with 40 pmol of each primer and the recommended concentrations of all other components of the kit, PCR is performed using the Peltier Thermal Cycler (PTC200; MJ Research, Watertown Mass.) and the following parameters:

| Step 1  | 94° C. for 1 min (initial denaturation) |
|---------|------------------------------------------|
| Step 2  | 65° C. for 1 min                         |
| Step 3  | 68° C. for 6 min                         |
| Step 4  | 94° C. for 15 sec                        |
| Step 5  | 65° C. for 1 min                         |
| Step 6  | 68° C. for 7 min                         |
| Step 7  | Repeat step 4–6 for 15 additional cycles |
| Step 8  | 94° C. for 15 sec                        |
| Step 9  | 65° C. for 1 min                         |
| Step 10 | 68° C. for 7:15 min                      |
| Step 11 | Repeat step 8–10 for 12 cycles           |
| Step 12 | 72° C. for 8 min                         |
| Step 13 | 4° C. (and holding)                      |

A 5–10 µl aliquot of the reaction mixture is analyzed by electrophoresis on a low concentration (about 0.6–0.8%) agarose mini-gel to determine which reactions were successful in extending the sequence. Bands thought to contain the largest products were selected and cut out of the gel. Further purification involves using a commercial gel extraction method such as QIAQuick™ (QIAGEN Inc). After recovery of the DNA, Klenow enzyme was used to trim single-stranded, nucleotide overhangs creating blunt ends which facilitate religation and cloning.

After ethanol precipitation, the products are redissolved in 13 µl of ligation buffer, 1 µl T4-DNA ligase (15 units) and 1 µl T4 polynucleotide kinase are added, and the mixture is incubated at room temperature for 2–3 hours or overnight at 16° C. Competent E. coli cells (in 40 µl of appropriate media) are transformed with 3 µl of ligation mixture and cultured in 80 µl of SOC medium (Sambrook J et al, supra). After incubation for one hour at 37° C., the whole transformation mixture is plated on Luria Bertani (LB)-agar (Sambrook J et al, supra) containing 2×Carb. The following day, several colonies are randomly picked from each plate and cultured in 150 µl of liquid LB/2×Carb medium placed in an individual well of an appropriate, commercially-available, sterile 96-well microtiter plate. The following day, 5 µl of each overnight culture is transferred into a non-sterile 96-well plate and after dilution 1:10 with water, 5 µl of each sample is transferred into a PCR array.

For PCR amplification, 18 µl of concentrated PCR reaction mix (3.3×) containing 4 units of rTth DNA polymerase, a vector primer and one or both of the gene specific primers used for the extension reaction are added to each well. Amplification is performed using the following conditions:

| Step 1 | 94° C. for 60 sec                         |
|--------|-------------------------------------------|
| Step 2 | 94° C. for 20 sec                         |
| Step 3 | 55° C. for 30 sec                         |
| Step 4 | 72° C. for 90 sec                         |
| Step 5 | Repeat steps 2–4 for an additional 29 cycles |
| Step 6 | 72° C. for 180 sec                        |
| Step 7 | 4° C. (and holding)                       |

Aliquots of the PCR reactions are run on agarose gels together with molecular weight markers. The sizes of the PCR products are compared to the original partial cDNAs, and appropriate clones are selected, ligated into plasmid and sequenced.

VI Labeling and Use of Hybridization Probes

Hybridization probes derived from SEQ ID NO:2 are employed to screen cDNAs, genomic DNAs or mRNAs. Although the labeling of oligonucleotides, consisting of about 20 base-pairs, is specifically described, essentially the same procedure is used with larger cDNA fragments. Oligonucleotides are designed using state-of-the-art software such as OLIGO 4.06 (National Biosciences), labeled by combining 50 pmol of each oligomer and 250 mCi of $[\gamma{-}^{32}P]$ adenosine triphosphate (Amersham, Chicago Ill.) and T4 polynucleotide kinase (DuPont NEN®, Boston Mass.). The labeled oligonucleotides are substantially purified with Sephadex G-25 super fine resin column (Pharmacia). A portion containing $10^7$ counts per minute of each of the sense and antisense oligonucleotides is used in a typical membrane based hybridization analysis of human genomic DNA digested with one of the following endonucleases (Ase I, Bgl II, Eco RI, Pst I, Xba 1, or Pvu II; DuPont NEN®).

The DNA from each digest is fractionated on a 0.7 percent agarose gel and transferred to nylon membranes (Nytran Plus, Schleicher & Schuell, Durham N.H.). Hybridization is carried out for 16 hours at 40° C. To remove nonspecific signals, blots are sequentially washed at room temperature under increasingly stringent conditions up to 0.1× saline sodium citrate and 0.5% sodium dodecyl sulfate. After XOMAT AR™ film (Kodak, Rochester N.Y.) is exposed to the blots in a Phosphoimager cassette (Molecular Dynamics, Sunnyvale Calif.) for several hours, hybridization patterns are compared visually.

VII Antisense Molecules

The sequence encoding HCP, or any part thereof, is used to inhibit in vivo or in vitro expression of naturally occurring sequence. Although use of antisense oligonucleotides, comprising about 20 base-pairs, is specifically described, essentially the same procedure is used with larger cDNA fragments. An oligonucleotide complementary to the coding sequence of HCP as shown in FIGS. 1, 2, 3 and 4 is used to inhibit expression of naturally occurring sequence. The complementary oligonucleotide is designed from the most unique 5' sequence as shown in FIGS. 1, 2, 3, and 4 and used either to inhibit transcription by preventing promoter binding to the upstream nontranslated sequence or translation of an HCP-encoding transcript by preventing the ribosome from binding. Using an appropriate portion of the leader and 5' sequence of SEQ ID NO:2 or SEQ ID NO:4 an effective antisense oligonucleotide includes any 15–20 nucleotides spanning the region which translates into the signal or early coding sequence of the polypeptide as shown in FIGS. 1, 2, 3, and 4.

VIII Expression of HCP

Expression of the HCP is accomplished by subcloning the cDNAs into appropriate vectors and transfecting the vectors into host cells. in this case, the cloning vector, pSport, previously used for the generation of the cDNA library is used to express HCP in E. coli. Upstream of the cloning site, this vector contains a promoter for β-galactosidase, followed by sequence containing the amino-terminal Met and the subsequent 7 residues of β-galactosidase. Immediately following these eight residues is a bacteriophage promoter useful for transcription and a linker containing a number of unique restriction sites.

Induction of an isolated, transfected bacterial strain with IPTG using standard methods produces a fusion protein which consists of the first seven residues of β-galactosidase, about 5 to 15 residues of linker, and the full length HCP. The signal sequence directs the secretion of HCP into the bacterial growth media which can be used directly in the following assay for activity.

IX Assay for HCP Activity

The characterization of protease activity and specificity is based on the rate of cleavage of specific peptide substrates and a determination of an inhibitor profile. Rates of cleavage for cathepsin L are assessed by incubation of the protease with substrates such as Z-Phe-Arg-AMC or Bz-Val-Lys-Lys-Arg-AFC and measuring the rate of release of the fluorescent or chromogenic leaving groups. Further specificity of the protease can be examined by titrating specific inhibitors into the cleavage assays and examining the change in the rate of proteolysis. Inhibitors for cathepsin L include trans-epoxysuccinyl-L-leucylamido-(3-methyl)butane, trans-epoxysuccinyl-L-leucylamido-(4-guanidino)butane, chymostatin, and PLCPI.

Rates of cleavage for cathepsin D are assessed by incubation of the protease with substrates such as D-Phe-Ser-(Bzl)-Phe-Phe-Ala-Ala-p-aminobenzoate and measuring the rate of release of the leaving group. Specificity of cathepsin D is confirmed by the effect of specific inhibitors including pepstatin A.

X Production of HCP Specific Antibodies

HCP substantially purified using PAGE electrophoresis (Sambrook, supra) are used to immunize rabbits and to produce antibodies using standard protocols. The amino acid sequence translated from HCP is analyzed using DNAStar software (DNAStar Inc) to determine regions of high immunogenicity and a corresponding oligopeptide is synthesized and used to raise antibodies by means known to those of skill in the art. Analysis to select appropriate epitopes, such as those near the C-terminus or in hydrophilic regions (shown in FIGS. 1, 4 and 7) is described by Ausubel FM et al (supra).

Typically, the oligopeptides are 15 residues in length, synthesized using an Applied Biosystems Peptide Synthesizer Model 431A using fmoc-chemistry, and coupled to keyhole limpet hemocyanin (KLH, Sigma) by reaction with M-maleimidobenzoyl-N-hydroxysuccinimide ester (MBS; Ausubel F M et al, supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radioiodinated, goat anti-rabbit IgG.

XI Purification of Naturally Occurring HCP Using Specific Antibodies

Naturally occurring or recombinant HCP are substantially purified by immunoaffinity chromatography using antibodies specific for HCP. An immunoaffinity column is constructed by covalently coupling HCP antibody to an activated chromatographic resin such as CnBr-activated Sepharose (Pharmacia Biotech). After the coupling, the resin is blocked and washed according to the manufacturer's instructions.

Membrane fractions from cells expressing HCP are prepared by methods well known in the art. Alternatively, a recombinant HCP fragment containing an appropriate signal sequence may be secreted in useful quantity into the medium in which transfected cells are grown.

An HCP-containing preparation is passed over the immunoaffinity column, and the column is washed under conditions that allow the preferential absorbance of HCP (eg, high ionic strength buffers in the presence of detergent). The column is eluted under conditions that disrupt antibody/HCP binding (eg, a buffer of pH 2–3 or a high concentration of a chaotrope such as urea or thiocyanate ion), and HCP is collected.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
       (A) LENGTH: 392 amino acids
       (B) TYPE: amino acid
       (C) STRANDEDNESS: single
       (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:

(vii) IMMEDIATE SOURCE:
       (A) LIBRARY: Consensus
       (B) CLONE: Consensus (xi) SEQUENCE DESCRIPTION: SEQ ID NO:1:

```
Met Val Cys Arg Leu Pro Val Ser Lys Lys Thr Leu Leu Cys Ser Phe
 1               5                  10                  15

Gln Val Leu Asp Glu Leu Gly Arg His Val Leu Leu Arg Lys Asp Cys
            20                  25                  30

Gly Pro Val Asp Thr Lys Val Pro Gly Ala Val Glu Pro Lys Ser Ala
            35                  40                  45

Phe Thr Gln Gly Ser Ala Met Ile Ser Ser Leu Ser Gln Asn His Pro
 50                  55                  60

Asp Asn Arg Asn Glu Thr Phe Ser Ser Xaa Ile Ser Leu Leu Asn Glu
65                  70                  75                  80

Asp Pro Leu Ser Gln Asp Leu Pro Val Lys Met Ala Ser Ile Phe Lys
            85                  90                  95

Asn Phe Val Ile Thr Tyr Asn Arg Thr Tyr Glu Ser Lys Glu Glu Ala
            100                 105                 110

Arg Trp Arg Leu Ser Val Phe Val Asn Asn Met Val Arg Ala Gln Lys
            115                 120                 125

Ile Gln Ala Leu Asp Arg Gly Thr Ala Gln Tyr Gly Val Thr Lys Phe
            130                 135                 140

Ser Asp Leu Thr Glu Glu Glu Phe Arg Thr Ile Tyr Leu Asn Thr Leu
145                 150                 155                 160

Leu Arg Lys Glu Pro Gly Asn Lys Met Lys Gln Ala Lys Ser Val Gly
            165                 170                 175

Asp Leu Ala Pro Pro Glu Trp Asp Trp Arg Ser Lys Gly Ala Val Thr
            180                 185                 190

Lys Val Lys Asp Gln Gly Met Cys Gly Ser Cys Trp Ala Phe Ser Val
            195                 200                 205

Thr Gly Asn Val Glu Gly Gln Trp Phe Leu Asn Gln Gly Thr Leu Leu
            210                 215                 220

Ser Leu Ser Glu Gln Glu Leu Leu Asp Cys Asp Lys Met Asp Lys Ala
225                 230                 235                 240

Cys Met Gly Gly Leu Pro Ser Asn Ala Tyr Ser Ala Ile Lys Asn Leu
            245                 250                 255
```

```
Gly Gly Leu Glu Thr Glu Asp Asp Tyr Ser Tyr Gln Gly His Met Gln
        260                 265                 270

Ser Cys Asn Phe Ser Ala Glu Lys Ala Lys Val Tyr Ile Asn Asp Ser
        275                 280                 285

Val Glu Leu Ser Gln Asn Glu Gln Lys Leu Ala Ala Trp Leu Ala Glu
290                 295                 300

Arg Gly Pro Ile Ser Val Ala Ile Asn Ala Phe Gly Met Gln Phe Tyr
305                 310                 315                 320

Arg His Gly Ile Ser Arg Pro Leu Arg Pro Leu Cys Ser Pro Trp Leu
                325                 330                 335

Ile Asp His Ala Val Leu Leu Val Gly Tyr Gly Asn Arg Ser Asp Val
                340                 345                 350

Pro Phe Trp Ala Ile Lys Asn Ser Trp Gly Thr Asp Trp Gly Glu Lys
        355                 360                 365

Gly Tyr Tyr Tyr Leu His Arg Gly Ser Gly Ala Cys Gly Val Asn Thr
370                 375                 380

Met Ala Ser Ser Ala Val Val Asp
385                 390

(2) INFORMATION FOR SEQ ID NO:2:

(i) SEQUENCE CHARACTERISTICS:
        (A) LENGTH: 1642 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(vii) IMMEDIATE SOURCE:
        (A) LIBRARY: Consensus
        (B) CLONE: Consensus (xi) SEQUENCE DESCRIPTION: SEQ ID NO:2:

GGCCACCCTG GAGGAGCCAC CCTGGAACGA CCCCATGGTG TGCCGGCTCC CCGTGTCCAA     60

GAAAACCCTG CTCTGCAGCT TCCAAGTCCT GGATGAGCTC GGAAGACACG TGCTGCTGCG    120

GAAGGACTGT GGCCCAGTGG ACACCAAGGT TCCAGGTGCT GTGGAGCCCA AGTCAGCCTT    180

TACTCAGGGC TCAGCCATGA TTTCTTCTCT GTCCCAAAAC CATCCAGACA ACAGAAACGA    240

GACTTTCAGC TCARTCATTT CCCTGTTGAA TGAGGATCCC CTGTCCCAGG ACTTGCCTGT    300

GAAGATGGCT TCAATCTTCA AGAACTTTGT CATTACCTAT AACCGGACAT ATGAGTCAAA    360

GGAAGAAGCC CGGTGGCGCC TGTCCGTCTT TGTCAATAAC ATGGTGCGAG CACAGAAGAT    420

CCAGGCCCTG GACCGTGGCA CAGCTCAGTA TGGAGTCACC AAGTTCAGTG ATCTCACAGA    480

GGAGGAGTTC CGCACTATCT ACCTGAATAC TCTCCTGAGA AAAGAGCCTG GCAACAAGAT    540

GAAGCAAGCC AAGTCTGTGG GTGACCTCGC CCCACCTGAA TGGGACTGGA GGAGTAAGGG    600

GGCTGTCACA AAAGTCAAAG ACCAGGGCAT GTGTGGCTCC TGCTGGGCCT TCTCAGTCAC    660

AGGCAATGTG GAGGGCCAGT GGTTTCTCAA CCAGGGGACC CTGCTCTCCC TCTCTGAACA    720

GGAGCTCTTG GACTGTGACA AGATGGACAA GGCCTGCATG GCGGCTTGC  CCTCCAATGC    780

CTACTCGGCC ATAAAGAATT TGGGAGGGCT GGAGACAGAG GATGACTACA GCTACCAGGG    840
```

-continued

```
TCACATGCAG TCCTGCAACT TCTCAGCAGA GAAGGCCAAG GTCTACATCA ATGACTCCGT    900

GGAGCTGAGC CAGAACGAGC AGAAGCTGGC AGCCTGGCTG GCCGAGAGAG GCCCAATCTC    960

CGTGGCCATC AATGCCTTTG GCATGCAGTT TTACCGCCAC GGGATCTCCC GCCCTCTCCG   1020

ACCCCTCTGC AGCCCTTGGC TCATTGACCA TGCGGTGTTG CTTGTGGGCT ACGGCAACCG   1080

CTCTGACGTT CCCTTTTGGG CCATCAAGAA CAGCTGGGGC ACTGACTGGG GTGAGAAGGG   1140

TTACTACTAC TTGCATCGCG GGTCCGGGGC CTGTGGCGTG AACACCATGG CCAGCTCGGC   1200

GGTGGTGGAC TGATGAGGGG CCCCCAGCTC GGGGCCTGGT GCTGATCAGA GTGGCTGCTG   1260

CCCCAGCCTG ACATGTGTCC AGGCCCCTCC CCGGGAGGTA CAGCTGGCAG AGGGAAAGGC   1320

ACTGGGTACC TCAGGGTGAG CAGAGGGCAC TGGGCTGGGG CACAGCCCCT GCTTCCCTGC   1380

ACCCCATTCC CACCCTGAAG TTCTGCACCT GCACCTTTGT TGAATTGTGG TAGCTTAGGA   1440

GGATGTCGGG GTTGAAGGGT GGTATCTTGG CAGTTGAAGC TGGGGCAAGA ACTCTGGGCT   1500

TGGGTAATGA AGCAGGAAGA AAATTTTCTT GATCTTAAGC CCACCTCTGT TCTGCCCCCC   1560

GCTTTTCCTC TGTTTGAATA CTATAAATTT TCTGGTTCCC TTTGGATTTA TGGATAAGTG   1620

TCCCCCTCCA TGTTCCAGGA AA                                            1642
```

(2) INFORMATION FOR SEQ ID NO:3:

(i) SEQUENCE CHARACTERISTICS:
        (A) LENGTH: 395 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:

(vii) IMMEDIATE SOURCE:
        (A) LIBRARY: LUNGNOT02
        (B) CLONE: 312099

(xi) SEQUENCE DESCRIPTION: SEQ ID NO:3:

```
Met Ser Pro Pro Leu Leu Gln Pro Leu Leu Leu Leu Pro Leu
 1               5                  10                  15

Leu Asn Val Glu Pro Ser Gly Ala Thr Leu Ile Arg Ile Pro Leu His
            20                  25                  30

Arg Val Gln Pro Gly Arg Arg Ile Leu Asn Leu Leu Arg Gly Trp Arg
        35                  40                  45

Glu Pro Ala Glu Leu Pro Lys Leu Gly Ala Pro Ser Pro Gly Asp Lys
    50                  55                  60

Pro Ile Phe Val Pro Leu Ser Asn Tyr Arg Asp Val Gln Tyr Phe Gly
65                  70                  75                  80

Glu Ile Gly Leu Gly Thr Pro Pro Gln Asn Phe Thr Val Ala Phe Asp
                85                  90                  95

Thr Gly Ser Ser Asn Leu Trp Val Pro Ser Arg Arg Cys His Phe Phe
            100                 105                 110

Ser Val Pro Cys Trp Leu His His Arg Phe Asp Pro Lys Ala Ser Ser
        115                 120                 125

Ser Phe Gln Ala Asn Gly Thr Lys Phe Ala Ile Gln Tyr Gly Thr Gly
    130                 135                 140
```

-continued

```
Arg Val Asp Gly Ile Leu Ser Glu Asp Lys Leu Thr Ile Gly Gly Ile
145                 150                 155                 160

Lys Gly Ala Ser Val Ile Phe Gly Glu Ala Leu Trp Pro Ser Leu
                165                 170                 175

Val Phe Ala Phe Ala His Phe Asp Gly Ile Leu Gly Leu Gly Phe Pro
                180                 185                 190

Ile Leu Ser Val Glu Gly Val Arg Pro Pro Met Asp Val Leu Val Glu
                195                 200                 205

Gln Gly Leu Leu Asp Lys Pro Val Phe Ser Phe Tyr Leu Asn Arg Asp
                210                 215                 220

Pro Glu Glu Pro Asp Gly Gly Leu Val Leu Gly Gly Ser Asp Pro
225                 230                 235                 240

Ala His Tyr Ile Pro Pro Leu Thr Phe Val Pro Val Thr Val Pro Ala
                245                 250                 255

Tyr Trp Gln Ile His Met Glu Arg Val Lys Val Gly Pro Gly Leu Thr
                260                 265                 270

Leu Cys Ala Lys Gly Cys Ala Ala Ile Leu Asp Thr Gly Thr Ser Leu
                275                 280                 285

Ile Thr Gly Pro Thr Glu Glu Ile Arg Ala Leu His Ala Ala Ile Gly
290                 295                 300

Gly Ile Pro Leu Leu Ala Gly Glu Tyr Ile Ile Leu Cys Ser Glu Ile
305                 310                 315                 320

Pro Lys Leu Pro Ala Val Ser Phe Leu Leu Gly Gly Val Trp Phe Asn
                325                 330                 335

Leu Thr Ala His Asp Tyr Val Ile Gln Thr Thr Arg Asn Asp Val Phe
                340                 345                 350

Leu Gly Thr Tyr Val Ala Val Phe Asp Arg Gly Asp Met Lys Ser Ser
                355                 360                 365

Ala Arg Val Gly Leu Ala Arg Ala Arg Thr Arg Gly Ala Asp Leu Gly
                370                 375                 380

Trp Gly Glu Thr Ala Gln Ala Gln Phe Pro Gly
385                 390                 395
```

(2) INFORMATION FOR SEQ ID NO:4:

(i) SEQUENCE CHARACTERISTICS:
      (A) LENGTH: 1299 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(vii) IMMEDIATE SOURCE:
      (A) LIBRARY: LUNGNOT02
      (B) CLONE: 312099

(xi) SEQUENCE DESCRIPTION: SEQ ID NO:4:

```
CCACGCGTCC GCAGCGATGT CTCCACCACC GCTGCTGCAA CCCCTGCTGC TGCTGCTGCC      60

TCTGCTGAAT GTGGAGCCTT CCGGGGCCAC ACTGATCCGC ATCCCTCTTC ATCGAGTCCA     120

ACCTGGACGC AGGATCCTGA ACCTACTGAG GGGATGGAGA GAACCAGCAG AGCTCCCCAA     180

GTTGGGGGCC CCATCCCCTG GGACAAGCC CATCTTCGTA CCTCTCTCGA ACTACAGGGA     240
```

```
TGTGCAGTAT TTTGGGGAAA TTGGGCTGGG AACGCCTCCA CAAAACTTCA CTGTTGCCTT    300

TGACACTGGC TCCTCCAATC TCTGGGTCCC GTCCAGGAGA TGCCACTTCT TCAGTGTGCC    360

CTGCTGGTTA CACCACCGAT TTGATCCCAA AGCCTCTAGC TCCTTCCAGG CCAATGGGAC    420

CAAGTTTGCC ATTCAATATG GAACTGGGCG GGTAGATGGA ATCCTGAGCG AGGACAAGCT    480

GACTATTGGT GGAATCAAGG GTGCATCAGT GATTTTCGGG GAGGCTCTCT GGGAGCCCAG    540

CCTGGTCTTC GCTTTTGCCC ATTTTGATGG GATATTGGGC CTCGGTTTTC CCATTCTGTC    600

TGTGGAAGGA GTTCGGCCCC CGATGGATGT ACTGGTGGAG CAGGGGCTAT TGGATAAGCC    660

TGTCTTCTCC TTTTACCTCA ACAGGGACCC TGAAGAGCCT GATGGAGGAG AGCTGGTCCT    720

GGGGGGCTCG GACCCGGCAC ACTACATCCC ACCCCTCACC TTCGTGCCAG TCACGGTCCC    780

CGCCTACTGG CAGATCCACA TGGAGCGTGT GAAGGTGGGC CCAGGGCTGA CTCTCTGTGC    840

CAAGGGCTGT GCTGCCATCC TGGATACGGG CACGTCCCTC ATCACAGGAC CCACTGAGGA    900

GATCCGGGCC CTGCATGCAG CCATTGGGGG AATCCCCTTG CTGGCTGGGG AGTACATCAT    960

CCTGTGCTCG GAAATCCCAA AGCTCCCCGC AGTCTCCTTC CTTCTTGGGG GGGTCTGGTT   1020

TAACCTCACG GCCCATGATT ACGTCATCCA GACTACTCGA AATGACGTCT TCTTGGGGAC   1080

GTATGTGGCC GTCTTCGACC GCGGGGACAT GAAGAGCAGC GCCCGGGTGG GCCTGGCGCG   1140

CGCTCGCACT CGCGGAGCGG ACCTCGGATG GGGAGAGACT GCGCAGGCGC AGTTCCCCGG   1200

GTGACGCCCA AGTGAAGCGC ATGCGCAGCG GGTGGTCGCG GAGGTCCTGC TACCCAGTAA   1260

AAATCCACTA TTTCCATTGA AAAAAAAAAA AAAAAAAA                           1299
```

We claim:

1. A substantially purified human cathepsin polypeptide comprising the amino acid sequence of SEQ ID NO:1, or immunologically active fragments thereof.

2. A pharmaceutical composition comprising a substantially purified human cathepsin protein having the amino acid sequence of SEQ ID NO:1 in conjunction with a suitable pharmaceutical carrier.

3. A method of treating cancer comprising administering to an individual in need of such treatment an effective amount of the pharmaceutical composition of claim 2.

* * * * *